(12) United States Patent
Chang et al.

(10) Patent No.: US 8,613,913 B2
(45) Date of Patent: Dec. 24, 2013

(54) SELF-MOLDING PERMANENT AGENT AND METHOD FOR PROCEEDING FREE-ROD AND FREE-BAND TYPE PERMANENT

(75) Inventors: Tae Sun Chang, Daejeon (KR); Dong Koo Lee, Daejeon (KR); Tae Soon Kim, Daejeon (KR); Wan Je Woo, Daejeon (KR)

(73) Assignee: Korea Research Institute of Chemical Technology (KR)

( * ) Notice: Subject to any disclaimer, the term of this patent is extended or adjusted under 35 U.S.C. 154(b) by 2000 days.

(21) Appl. No.: 11/192,287

(22) Filed: Jul. 29, 2005

(65) Prior Publication Data

US 2006/0024257 A1  Feb. 2, 2006

(30) Foreign Application Priority Data

Jul. 30, 2004 (KR) .................. 10-2004-0060543
Jul. 30, 2004 (KR) .................. 10-2004-0060544

(51) Int. Cl.
*A61K 8/00* (2006.01)
*A61K 8/18* (2006.01)
*A61Q 5/04* (2006.01)
*A61K 8/19* (2006.01)
*A61K 8/58* (2006.01)

(52) U.S. Cl.
USPC ........................ 424/70.2; 424/70.4

(58) Field of Classification Search
USPC .............................. 424/70.2, 70.4
See application file for complete search history.

(56) References Cited

U.S. PATENT DOCUMENTS 5,165,427 A * 11/1992 Borish .................. 132/204
5,988,180 A * 11/1999 Bergstrom .............. 132/204
6,004,355 A * 12/1999 Dias et al. ................. 8/406
6,146,619 A * 11/2000 Cortekar et al. ......... 424/70.1

FOREIGN PATENT DOCUMENTS

FR  2675379  * 4/1996 .............. A61K 8/46

OTHER PUBLICATIONS

Translation of DE 102004049093, Walter Andrea, Oct. 2004.*
Omidian et al. (Macromol. Biosci., 2006, 6, 703-710).*

* cited by examiner

*Primary Examiner* — Fereydoun G Sajjadi
*Assistant Examiner* — Genevieve S Alley
(74) *Attorney, Agent, or Firm* — Finnegan, Henderson, Farabow, Garrett & Dunner, LLP

(57) ABSTRACT

The present invention relates to a self-molding permanent agent and a method for proceeding free-rod and free-band type permanent, more particularly to a self-molding permanent agent comprising (a) a reducing composition containing a reducing agent reducing a disulfide bond of cystine on the hair and a molding stimulant spontaneously molding to fix a hair design; (b) a molding composition inducing to mold after reacting with the molding stimulant; and (c) a softening composition releasing the action of a molding stimulant, and a method for pressing a free-rod and free-band type permanent, which overcomes a disadvantage in the conventional method for pressing a permanent that needs to wear a curling device such as rods for a permanent (perm rod) or rubber band and improves to apply a wave set without a hair-curling device for a short time, since it has a self-molding feature.

61 Claims, 4 Drawing Sheets

SELF-MOLDING PERMANENT AGENT AND METHOD FOR PROCEEDING FREE-ROD AND FREE-BAND TYPE PERMANENT

TECHNICAL FIELD

The present invention relates to a self-molding permanent agent and a method for proceeding free-rod and free-band type permanent, more particularly to a self-molding permanent agent comprising (a) a reducing composition containing a reducing agent reducing a disulfide bond of cystine on the hair and a molding stimulant spontaneously molding to fix a hair design; (b) a molding composition inducing to mold after reacting with the molding stimulant; and (c) a softening composition releasing the action of a molding stimulant, and a method for pressing a free-rod and free-band type permanent, which overcomes a disadvantage in the conventional method for pressing a permanent that needs to wear a curling device such as rods for a permanent (perm rod) or rubber band and improves to apply a wave set without a hair-curling device for a short time, since it has a self-molding feature.

BACKGROUND ART

Permanent agent is a composition used to set a hair design maintained for a long time. In general, permanent agent is often comprised of a reducing agent that reduces a disulfide bond of cystine when it is applied to the hair and an oxidizing agent that oxidizes the disulfide bond to reset hair in a desired mode after treating the reducing agent and to fix the hair design.

For a reducing agent of permanent agent, thiol, sulfide, bisulfide or the like are often utilized. Precisely, the reducing gent can be selected from the group consisting of cysteine and its derivative, cysteamine and its derivative, thiolactic acid, thioglycolic acid and its ester or alkali salt and glyceryl thioglycolate. Especially, thioglycolic acid alkali salt is reported to be most effective among the reducing agents and is a universal component of a reducing agent included in a permanent agent.

Several techniques relating to a permanent agent have been disclosed as follows.

The hair treatment agent of keratin fiber that is encapsulated by polyvinyl alcohol to sustain various constituents preventing a hair injury is disclosed in Korean Patent Laid-open No. 2001-0033091. Also, the method for mixing other components such as polyvinyl pyrrolidone, surface-active agent and extender for viscosity in a permanent agent to retain the setting function of hair styling agent such as mousse, spray, gel and glaze as well as the permanent press function on the hair, is demonstrated in Korean Pat. No. 0167487.

In addition, the permanent agent and straightening agent wherein stable beads in the reductive agent 1 and the oxidative agent 2 containing a hair nutrient component are dispersed to decrease hair injury and scalp irritation, to enhance the sustainability and not to be affected by heating and the method for preparing the same are disclosed in Korean Pat. No. 0405955. Besides, the permanent composition comprising ceramide, cysteine and phospholipid and the method for applying a permanent set by combining hair shampoo, treatment agent, oxidant, rinse, cuticle modulator with the same, are illustrated in Korean Patent Laid-open No. 2002-0021141. Also, the process for washing hair by using shampoo containing ceramide; the process for providing a treatment agent containing ceramide on the hair; and the method for pressing a permanent comprising steps (1) setting hair by using a permanent press composition and (2) treating an oxidant are disclosed. Furthermore, the method for pressing a permanent wherein a multiple system using one more substance among two soluble agents and a rinse product is adopted as a chemical suitable for the reductive reaction of keratin fiber and the persistent oxidative reaction, is demonstrated in Korean Patent Laid-open No. 2002-0021392. Herein, oil component and alcohol are defined and a conditioning agent is also included. In addition, the method for treating keratin to reset the hair permanently, wherein for a stable reducing agent comprising a solid composition in a powder form and a liquid composition, cysteine, cysteamine or the like are mixed to maintain the stability and the efficacy of a reducing agent, even if other reducing agent becomes unstable and ineffective and for a solid carrier, silica, clay, carbohydrate and organic polymer are selected, is already illustrated in Korean Pat. No. 0411960.

Generally, a method for pressing a permanent by using a permanent agent mentioned above is proceeded as follows.

In the first step, a reducing composition containing a reducing agent is treated to dissociate a disulfide bond of keratin (i.e., cystine).

In the second step, a curling device such as rods for a permanent press (hereinafter, referred to as "perm rod") or other means are equipped to set hair by tensile force after dissociating a disulfide bond.

In the third step, an oxidizing composition (also referred to as "neutralizing agent") is added on the hair curled above to rearrange the disulfide bond and finally, maintain the hair in a desired mode.

By the process for pressing a permanent described above, the hair can be curled, straightened, untied to remove a curl or waved smoothly. In this procedure, a hair-curling apparatus such as perm rod and rubber band can be exploited to fix hair in an intended mode, or a vinyl cap can be used to prevent the evaporation of moisture from a reducing composition or an oxidizing composition.

However, there are some disadvantages in the conventional process for pressing a permanent as follows.

First, this procedure may be dangerous to drop out hairs or cause red spots on the scalp, because hair is pulled down and set forcibly and elongate a disulfide bond of cystine to decrease the elastic strength of hair, break hair easily and injure the hair.

Second, it may leave a rod track because a hair-curling device are equipped as compressing by mechanical force and carve a rubber band track on the hair because a rubber band is placed on the hair to fix a perm rod. As a result, the hair is cut and hurt at the track to interfere a wave set in a desired mode.

Third, it cannot apply a natural wave set on the hair because a forcible permanent wearing a hair-curling device such as perm rod and rubber band makes an artificial curl.

Fourth, it may cause a severe hair injury by a permanent agent since at least 40 minutes is required to curl hair and is inconvenient and painful to spend more than 40 minutes while wearing a curling device.

Fifth, it cannot apply a wave set on the hair without rods.

The permanent agents and methods for performing a permanent press described above have been utilized for 80 years, but are seldom improved and displaced in spite of such a problem. Even reformed product does not outgrow the conventional process remarkably, although it adopted a surface-active agent or the like in a straightening agent to apply a straight wave. Therefore, it is necessary that the permanent agent developed presently should utilize a curling device such as perm rod or rubber band to fix hair to an intended design.

On the other hand, the hair setting agent comprising solution 1 containing polysaccharide and solution 2 containing metal salts reacting with the polysaccharide and gelling, is elucidated in Japanese Unexamined Pat. No. 2000-191478. Unfortunately, it just described the process for setting hair temporarily after coating by the gel reaction of polysaccharide or the technique for attaching a decoration on the hair. That is to say, the hair styling product that applies a wave set disappearing during styling or shampoo-washing and induces to reset hair temporarily are clarified in Japanese Unexamined Pat. No. 2000-191478. This product is clearly discriminated from the permanent agent of the present invention that maintains a hair design for several weeks after treatment and does not change a wave set even if washing hair by water or shampoo.

DISCLOSURE OF INVENTION

In order to settle above-mentioned problems, the present inventors have tried to develop a novel a permanent agent and a method for performing a permanent press that improves the existed permanent agent and method for pressing a permanent.

Precisely, the present invention has been developed a newly-conceptual process for proceeding a permanent wherein a molding stimulant that has the physicochemical property to mold spontaneously for setting a hair and release the molding by adding a softening agent, is coordinated with some constituents of a reducing agent to design hair in a desired mode without a curling device and completed successfully.

Therefore, the object of the present invention is to provide a self-molding permanent agent that can design hair in a desired mode without a hair-curling device for a short time, since it has a feature to mold spontaneously.

In addition, the object of the present invention is to provide a method for proceeding free-rod and free-band type permanent without a hair-curling device to apply a wave set on the hair for a short time.

Additional advantages, objects and features of the present invention will be set forth in part in the description which follows and in part will become apparent to those having ordinary skill in the art upon examination of the following or may be learned from practice of the invention.

It is natural that other objects and advantages of the invention may be realized and attained by the structure particularly pointed out in the written description and claims hereof as well as the appended drawings.

BRIEF DESCRIPTION OF THE DRAWINGS

The above and other objects, features and other advantages of the present invention will be more clearly understood from the following detailed description taken in conjunction with the accompanying drawings, wherein.

BEST MODE FOR CARRYING OUT THE INVENTION

Figure 1:
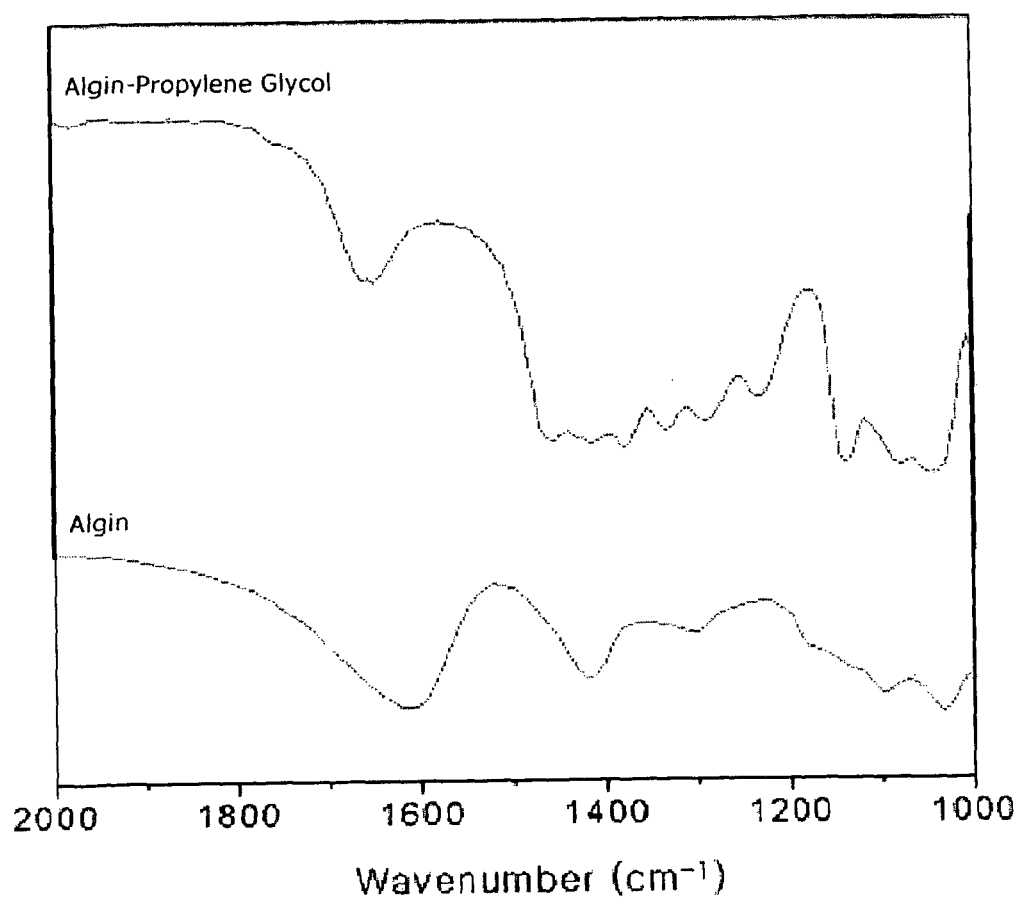
FIG. 1 illustrates infrared (IR) spectroscopic data of the molding product that is comprised of 2 weight % of algin as a molding stimulant and 3 weight % of propylene glycol as a reactive substance and reacted with a bivalent metal element.

The present invention provides a permanent agent for self-molding comprising: (a) a reducing composition containing a reducing agent and a molding stimulant; (b) a molding composition inducing to mold after reacting with the molding stimulant; and (c) a softening composition releasing the action of a molding stimulant.

In addition, the present invention provides a method for pressing a permanent in a free-rod and free-band type, which comprises steps:

(1) coating a reducing composition comprising a reducing agent and a molding stimulant on the hair;
(2) curling hair coated with the reducing composition;
(3) coating a molding composition inducing to mold after reacting with the molding stimulant, on the hair curled above to mold the hair;
(4) coating a softening composition on the hair molded above to stop the molding action; and
(5) washing hair coated with the softening composition.

Hereinafter, the present invention will be described more clearly as follows.

The present invention has a most remarkable feature in the technique to confer the self-molding ability for a permanent agent by using a molding stimulant as a main component that can mold any object having some elasticity and hardness and release the molding step by adding a constituent dissociating the chemical bond of object. Therefore, the permanent agent of the present invention can apply a wave set in a desired mode for a short time, without an additional device for hair-curling.

Besides, the molding stimulant of the present invention can be selected from organic substance that is affinitive for a living body to give nutrients on the hair and forms an organic/inorganic complex membrane having IPN (interpenetrating polymer network) internal structure. The molding reaction forming an organic/inorganic complex can stimulate the hair setting by self-generating heat without any other treatment so as to curtail a time period for setting hair, since it is a fundamentally exothermic reaction.

The present invention has a technical feature to modulate the viscosity of permanent agent as well as the pore size within IPN internal structure by adding a reactive substance reacting with the molding stimulant. The IPN internal structure may be produced during a molding process by the action of a molding stimulant and include pores to transport solid and liquid substance through this pore channel. In the present invention, the pore size is controlled by adding a reactive substance to the molding stimulant additionally so as to supplement a reducing agent, nutrients and the like on the hair rapidly, which can reduce the time period for performing a permanent press, decrease the probability of hair injury and further, provide nutrients easily to gloss the hair. Besides, the viscosity of permanent agent can be modulated by a reactive substance, depending upon its nature and content. In the present invention, the reactive substance can be used as a modulator of viscosity to design hair without an additional curling device.

In addition, the present invention has another technical feature to adopt a nano-sized metal component as a reduction catalyst and an oxidizing catalyst that stimulate the reductive reaction for dissociating a disulfide bond of cystine in hair and the oxidative reaction for restoring the disulfide bond. It is known that metals are different in the physicochemical property according to particle size, since the ratio between atomic number in a particle and atomic number on the surface changes. In the present invention, a metal catalyst is a powder or in a liquid of nano-size to prepare a permanent agent so that the catalytic activity is enhanced by adjusting the size of metal particle and further, nutrients are provided easily on the hair because of its natural property.

Preferably, the nano-sized metal catalyst of the present invention can be "metal colloid" that is a solution form prepared by dispersing metal micro-particles of nano-size into a solution. The metal colloid may be manufactured by well-known procedures and is prepared in the present invention as follows. In the first process for preparing a metal colloid, a metal precursor solution and a reducing agent solution are prepared respectively, mixed and stirred at room temperature or in the temperature range of boiling point of solvent. In the second process for preparing a metal colloid, a hydrochloric acid solution is added to a metal precursor solution and stirred at room temperature or in the temperature range of boiling point of solvent. The particle size of metal colloid prepared above can vary, depending upon temperature and stirring velocity. Preferably, the size of metal particle is several or hundreds of nanometer and more preferably, 10~100 of nanometers. High frequency generator, ultrasonic vibrator, nozzle sprayer or the like can be applied properly to scatter the nano-sized particles of metal mentioned above homogeneously in a colloidal solution. The metal precursor preparing metal colloid can be a nitric acid salt, acetic acid salt, hydrochloric acid salt or hydroxide of metal. The solvent for preparing a colloidal solution can be a solvent dissolving a metal precursor and selected according to a metal precursor.

Preferably, the solvent can be one or a mixture selected from the group consisting of water, alcohols having 1~10 of carbon number, ketones, aldehydes, acids and the like. The reducing agent can be selected from the group consisting of glucose, hydrazine, borohydride compound, dimethylaminoborane, citric acid salt and the like. At this moment, dispersion stabilizer, reducing stabilizer or the like can be selected to disperse the solution easily or to help a metal precursor reduced, if necessary. The dispersion stabilizer can be any surface-active agent that belongs to anionic system, cationic system or nonionic system ordinarily used in this art and preferably, polyvinyl pyrrolidone as a surface-active agent of nonionic system. Also, the reducing stabilizer can be any one selected from the group consisting of ethylene glycol, glycine, dextrose or the like ordinarily used in this art and preferably, dextrose.

The molding product prepared after coating hair by the permanent agent of the present invention, is a sheer and hardened membrane having IPN internal structure plays a role to isolate a reducing agent from outer environment. As a reference, the reducing composition is protected by wearing a vinyl cap and not dried after coating on the hair in conventional methods for pressing a permanent. The permanent agent of the present invention can be used without wearing a vinyl cap. It is natural that a vinyl cap may be used to keep warm and separate outer environment thoroughly. The molding membrane having IPN internal structure continues to transport a reducing agent and a hair treatment agent on the hair through the pore channel, since it has a lot of pores, which can enhance the reductive power so as to apply a hair wave for a short time. Especially, the membrane of molding product has some extent of viscosity, adhesiveness and hardness, which facilitates a wave set of hair, maintains a hair mode long and molds hair without an additional device for hair-curling.

The permanent agent of the present invention can be a 3-solution type agent comprising (a) a reducing composition; (b) a molding composition; and (c) a softening composition; or a 4-solution type agent comprising the same and an additional oxidizing composition containing an oxidant. That is to say, any permanent agent comprising as an essential composing (a) a reducing composition containing a reducing agent and a molding stimulant; (b) a molding composition forming organic/inorganic complex membrane after reacting with the molding stimulant; and (c) a softening composition releasing the action of molding, can be within the scope of the present invention.

Hereinafter, the permanent agent of the present invention will be described more clearly, aiming to each component, its application and principle thereof.

Above all, the reducing composition (a) is prepared by adding a reducing agent and a molding stimulant as an essential component.

As an essential constituent of the reducing composition, a reducing agent can be any substance ordinarily used in this art. Preferably, the reducing agent has a functional group selected from the group consisting of sulfide, bisulfide, thiol, cyanide, thiocyanide, hydroxide, sulfite, bisulfite and bicarbonate and more preferably, one or a mixture selected from the group consisting of thioglycolic acid or its salt, thioglycolic acid ester, thiolactic acid, thiolactic acid ester, cysteine, cysteamine, thiocyanide, sulfite and their derivative. The derivative can be a salt suitable for a cosmetic use and preferably hydrochloric acid salt, bromic acid salt, citric acid salt, acetic acid salt, sulfuric acid salt or the like. The reducing agent can be added to the reducing composition (a) in the range of 1~25 weight %. If the content of a reducing agent is less than 1 weight %, the disulfide bond of hair cystine is not reduced properly. In contrast, if the content of a reducing agent is over 25 weight %, the hair is problematically injured. Preferably, the reducing agent can be added to the reducing composition (a) in the range of 2~20 weight %.

As another essential constituent, the reducing composition (a) of the present invention includes a molding stimulant. The molding stimulant is made to an organic/inorganic complex membrane having the elasticity and the hardness in some extent. In the present invention, the molding stimulant is utilized to fix a wave on the hair IPN and excludes to use a hair-curling device. Besides, the molding product that is prepared after the stimulant molds, forms a coating membrane network-structured on the surface of hair to block a permanent agent from outer environment, which prevents the evaporation of reducing composition and transports oxygen gas, reducing agent, hair treatment agent and the like on the hair while passing the cavity in a network structure for a short time period and consistently, since gas or liquid can penetrate easily through pores existing in the network structure. Further, the molding stimulant reduces the time required for a hair design remarkably, and prevents a hair injury and rather gives nutrients on the hair.

The molding stimulant added to the reducing composition (a) can be any kind of substance preparing a molding product having some extent of elasticity and hardness. Preferably, the molding stimulant can be a chemically stable substance that is not affected by a constituent of permanent agent, especially by a reducing agent and more preferably, a substance that does not influence the permanent press. The molding stimulant can be one or a mixture selected from the group consisting of algin, alginic acid, alginate, alginic acid salt and their derivatives. At this moment, the derivative can contain at least one functional group selected from the group consisting of univalent or multivalent hydroxyl group, aldehyde group, carboxylic acid group, carboxylate group, ketone group and the like. The molding stimulant can be added to the reducing composition (a) in the range of 0.1~15 weight %. If the content of a molding stimulant is less than 1 weight %, the permanent agent does not have the molding property. If the content of a molding stimulant is more than 15 weight %, it becomes hard before molding hair in a desired mode since it reduces the time required for molding problematically. Preferably, the molding stimulant can be added to the reducing composition (a) in the range of 0.5~10 weight %.

In the reducing composition (a) of the present invention, a reactive substance having a functional group reacting with the molding stimulant can be added. That is to say, the reactive substance having at least one functional group selected from the group consisting of hydroxyl (—OH), carboxylic acid (—COOH), carboxylate (—COOR), ketone(—CO) and aldehyde (—COH) that can all react with a molding stimulant such as algin, alginic acid, alginate, alginic acid salt and their derivative. The reactive substance added in the reducing composition (a) can modulate the pore size of network structure in the molding product, control the penetration velocity of gas or liquid, adjust the viscosity as a controller to apply a wave set, and help hair fixed in a curled state. Preferably, the reactive substance has the molecular weight in the range of 50~10,000. The reactive substance in the reducing composition (a) adjusting the pore size in the network structure of molding product can be selected from the group consisting of polyols including glycol, polyalkylene glycol, polyvinyl alcohol, chitin or chitin derivative, chito acid or chito acid derivative, maleic acid, aminopropyl-silicic acid, poly-L-lysine, cellulose, cellulose salt or their derivative, adipic acid, gelatin, pectin, arginine or their polymer, gluconic acid, lactone, sodium caseinate, vinyl acetate, starch or their derivative, elastin, acrylamide, acrylamide polymer or their derivatives, gelan gum, carbopol, glutaraldehyde, and acrylate polymer. Preferably, the reactive substance can be selected from the group consisting of polyalkylene glycol, chito acid and maleic acid and utilized solely or coordinately. The reactive substance can be added to the reducing composition (a) in the range of 0~5 weight %. If the content of reactive substance is over 5 weight %, the permanent agent cannot control the viscosity and mold hair effectively, since the molding stimulant decreases in the content relatively. Preferably, the reactive substance can be added to the reducing composition (a) in the range of 0.01~3 weight %.

FIG. 1 illustrates infrared (IR) spectroscopic data of the molding product that is reacted with algin as a molding stimulant and propylene glycol as a reactive substance. As shown in FIG. 1, a peak corresponding to a conjugated ester bond formed by reacting algin and propylene glycol at 1,600~1,700 cm$^{-1}$. As a result, this bond energy is lowered after the reaction, comparative to the bond energy of carbonyl group (C=O) of algin before the reaction. It is concluded that this data should demonstrate the change of bond energy in an oxide group of propylene glycol. The chemical formula of conjugated ester bond formed by reacting algin and propylene glycol is illustrated as follows.

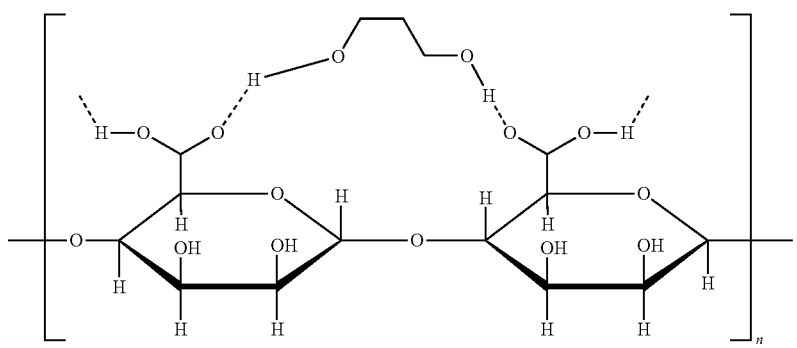

Besides, the reducing composition (a) of the present invention can include a reduction catalyst additionally.

The reduction catalyst of the present invention can be metal selected from the group consisting of gold, platinum, palladium, rhodium, hydrides, hydroxides, oxalic acid and ascorbic acid or metal compound and utilized solely or coordinately in a mixture. The metal and metal compound can be used as a reduction catalyst in a powder or liquid form of nano-size. The reduction catalyst of nano-sized metal enhances the reaction when it is added to the reducing composition, dissociates a disulfide bond rapidly, decreases a hair injury maximally and reduces the time required for pressing a permanent remarkably. In addition to metal and metal compound, the reducing composition (a) of the present invention can include hydride, hydroxide, oxalic acid, ascorbic acid and the like as a reduction catalyst additionally.

The reduction catalyst can be added to the reducing composition (a) in the range of 0~5 weight %. If the reduction catalyst is used over 5 weight %, the reaction is not economical because the catalytic activity is not increased. Preferably, the reduction catalyst can be added to the reducing composition (a) in the range of 0.0001~5 weight %.

In the reducing composition of the present invention, polymer, amino acid, alkalinizing agent, glycols, chelate compound, surface-active agent and any other treatment agent can be added if it does not affect the reductive property when used ordinarily. Preferably, the amino acid can be selected from guanine, hydrolyzed keratin (PPT) and the like. Preferably, the alkalinizing agent can be selected from the group consisting of monoethanolamine, diethanolamine, triethanolamine, isopropanolamine, 2-methyl-2-amino-1-propanol, 1,3-propanediamine, ammonium, organic carbonate such as alkali metal carbonate, bicarbonate and guanidine carbonate or alkali metal hydroxide and is used solely or coordinately in a mixture. The surface-active agent can be any substance used ordinarily for a reducing composition of permanent press and any surface-active agent belonging to anionic system, cationic system or nonionic system can be adopted. Preferably, the nonionic surface-active agent can be selected from the group consisting of alkyl ammonium salt, alkyl sulfate, alkyl benzene sulfate, alkyl ether sulfate, alkyl sulfonate, tetravalent ammonium salt, alkyl beteine, oxyethylene alkyl phenol, fatty acid alkanol amide, oxyethylene fatty acid ester and hydroxypropyl ether system. Other treatment agent can be volatile or non-volatile and selected from the group consisting of linear or circular silicon or its mixture, polydimethyl siloxane, tetravalent polyorgano siloxane, polydimethyl siloxane-polyoxyalkyl copolymer such as dimethicone copolyol, polydimethyl siloxane containing a terminal group of stearoxy-(stearoxydimethicone), polydimethylsiloxane dialkyl ammonium acetate copolymer or polydimethylsiloxane polyalkyl beteine copolymer, polysiloxane reformed by mercapto or mercapto alkyl group or silane such as stearoxyltrimethylsilane. In addition, wax and an expansion agent, a penetration agent or the like can be added to strengthen the activity of a reducing agent and to harden a molding stimulant. Various constituents used for a reducing agent of ordinary permanent agent can be adopted. Preferably, dimethylisosorbitol, urea and its derivative, pyrrolidone, n-alkylpyrrolidone, thiamorpholine, alkylene glycol or alkyl ether of dialkylene glycol such as propylene glycol monomethyl ether or dipropylene glycol monomethyl ether, alkanediols in 3~6 of carbon number such as 1,2-propanediol, 2-imidazolidione, fat alcohol, lanoline derivative, ceramide, especially glycoceramide, pseudoceramide and the like, active constituent such as pantothenic acid, preventive agent of hair loss, dandruff preventive agent, suspension agent, metal ion blocker, turbidity agent, coloring agent, sun blocker, aromatic, conservative and the like can be adopted. Further, amino acid, polypeptide, ceramide, minerals, keratin and the like can be selected. It is natural that the additive described above can be selected easily by those skilled in this art since it is an ordinary component to prepare a permanent agent. The additive can be used to the reducing composition (a) in the range of 0~70 weight %. If the additive is used over 70 weight %, the contents of a reducing agent and a molding stimulant decrease relatively, which interfere with preparation of the self-molding permanent of the present invention. Preferably, the additive can be used to the reducing composition (a) in the range of 0.01~60 weight %.

The reducing composition (a) of the present invention can be prepared by adding a molding stimulant to commercially available permanent agent 1 containing a reducing agent. The permanent agent 1 used in the present invention is a processing solution that dissociates a chemical bond of keratin (cystine) as an essential component of hair and should include a reducing agent or a reductive substance.

The commercial permanent agent 1 is adjusted in dose by the content of a reducing agent. The permanent agent 1 can be added to the reducing composition (a) in the range of 10~98.9 weight %. If commercial permanent agent 1 is added less than 10 weight %, the disulfide bond of hair cannot dissociate due to lack of a reducing agent content. In contrast, if permanent agent 1 is added over 98.9 weight %, the molding stimulant decreases in the content relatively, which interfere with the molding action. Preferably, the permanent agent 1 can be added to the reducing composition (a) in the range of 50~98 weight %.

The reducing composition (a) of the present invention can be prepared by mixing each constituent described above in deionized water and made to a gel or sol form. The reducing composition (a) is adjusted to have the range of pH 4~11. If the reducing composition is less than pH 4 or over pH 11, the disulfide bond of hair does not dissociate and hair is injured and not molded properly. Preferably, the reducing composition can be adjusted to have the range of pH 5.5~9.5.

The reducing composition (a) of the present invention comprises in the content ratio as follows: 2~20 weight % of a reducing agent (preferably, 2~20 weight %); 0.1~15 weight % of a molding stimulant (preferably, 0.5~10 weight %); 0~5 weight % of reactive substance (preferably, 0.01~3 weight %); 0~5 weight % of reduction catalyst (preferably, 0.0001~5 weight %); 0~70 weight % of other additive (preferably, 0.01~60 weight %); and 1~98.9 weight % of deionized water (preferably, 30~90 weight %).

In the reducing composition (a) of the present invention, commercial permanent agent 1 can be adopted to replace a reducing agent and other additive. At this moment, the reducing composition (a) comprises in the content ratio as follows: 10~98.9 weight % of permanent agent 1 (preferably, 50~98 weight %); 0.1~15 weight % of a molding stimulant (preferably, 0.5~10 weight %); 0~5 weight % of reactive substance (preferably, 0.01~3 weight %); 0~5 weight % of reduction catalyst (preferably, 0.0001~5 weight %); and 1~89.9 weight % of deionized water (preferably, 1~70 weight %).

The self-molding permanent agent of the present invention can be prepared, when the reducing composition (a) comprises a molding stimulant and a reactive substance in the range of 1:0.01~1 weight ratio and cannot be manufactured, when the content ratio is not maintained. Especially, the reactive substance can be an essential component in the range described above to control the physical property of permanent agent including viscosity, adhesiveness and hardness controlled easily within a desired range.

Figure 2:
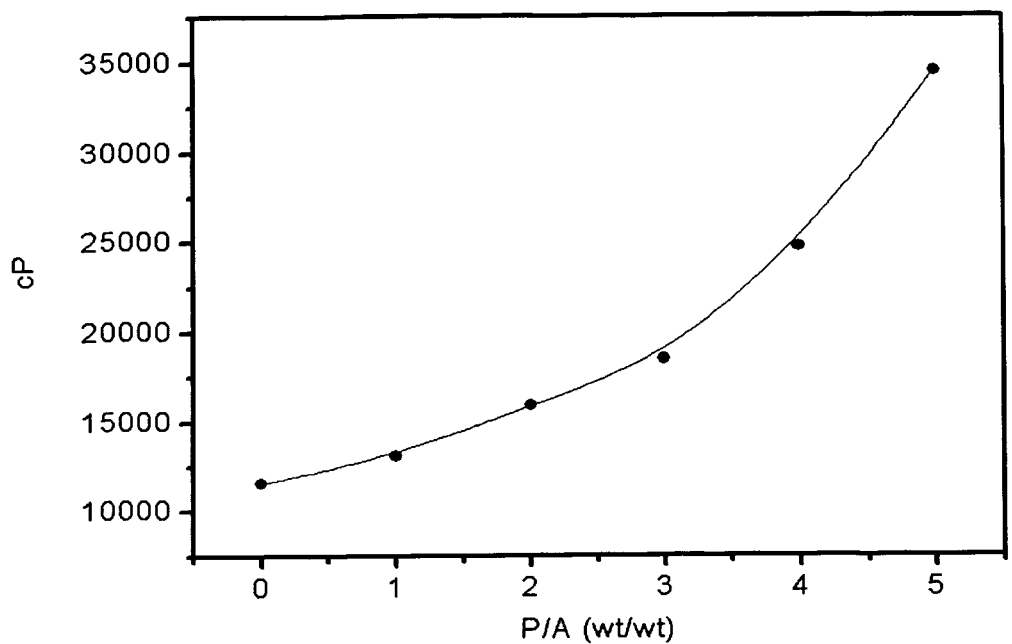
FIG. 2 illustrates the change of viscosity in permanent agents according to weight ratio of algin as a molding stimulant and propylene glycol as a reactive substance.

In order to self-mold hair and apply a wave set for a short time, it is important to adjust the viscosity of the reducing composition (a) in the present invention. Preferably, the reducing composition (a) can sustain the viscosity in the range of 6,000~60,000 cP to produce the self-molding permanent agent and more preferably, in the range of 10,000~50,000 cP. The viscosity of the reducing composition (a) can be often controlled by a molding stimulant, a reactive substance and its content ratio. FIG. 2 illustrates the change of viscosity in a permanent agent according to weight ratio of algin as a molding stimulant and propyleneglycol as a reactive substance. As a result, it is confirmed that the reducing composition (a) having a proper viscosity satisfying the purpose of the present invention can be comprised of algin and propylene glycol in the range of 1:0~5 weight ratio.

Second, the molding composition (b) of the present permanent agent is combined with a molding stimulant of the reducing composition (a) agent to induce the molding action.

The molding composition (b) reacts with a molding stimulant to induce the molding and can include bivalent metal element as an essential component. In the present invention, the bivalent metal element can be any producing $M^{2+}$ ion and selected from metal, metal compound, their soluble salt or the like. As a reference, univalent or trivalent metal element can be also adopted to induce the molding action by a molding stimulant, but $M^+$, $M^{3+}$ and $M^{6+}$ metals including uranium ($U^{6+}$), cesium ($Cs^+$), rubidium ($Rb^+$) and iron (III) ($Fe^{3+}$) are not suitable for the molding composition, since they may decrease the reductive power of reducing composition, interfere to apply a wave set and cause a hair injury. Accordingly, bivalent metal element including magnesium (Mg), calcium (Ca), barium (Ba), zinc (Zn), strontium (Sr) and iron (II) (Fe) can be selected as an effective component of a molding stimulant that induces to mold. The use of metal element is another technical feature of the present invention. Preferably, the bivalent metal can be selected from the group consisting of magnesium hydroxide, barium chloride, strontium chloride, calcium hydroxide, calcium chloride, calcium acetate, magnesium chloride and the like. Any compound derived from the same can be selected solely or coordinately. The bivalent metal element mentioned above can be added to the molding composition (b) of the present invention in the range of 0.1~25 weight %. If the content of bivalent metal is less than 0.1 weight %, the molding stimulant is not effective sufficiently to mold the hair. In contrast, if the content of bivalent metal is over 25 weight %, the next softening step is not accomplished easily and the reductive power decreases. Preferably, the bivalent metal mentioned above can be added to the molding composition (b) of the present invention in the range of 1~20 weight %.

In the molding composition (b) of the present invention, other substance used ordinarily for a permanent agent can be also added and selected from the group consisting of reducing supplement, penetration agent, moisturizer, an expansion agent, hardening supplement, surface-active agent, alkalinizing agent, acidifying agent, glycols, chelate compound or the like. Further, hair nutrient such as amino acid, polypeptide, ceramide, minerals, keratin can be added. Preferably, the reducing supplement can be selected from the group consisting of iron system compound, alcohol, glycol, glycol ester, urea and pyrrolidone and used solely or coordinately in a mixture. The penetration agent and the expansion agent are used to help the hardening agent permeate and the hardening supplement is used to enhance the molding action. It is natural that the additive described above can be selected easily by those skilled in this art, since it is an ordinary component to prepare a permanent agent. The additive can be added to the molding composition (b) in the range of 0~30 weight %. If the additive is over 30 weight %, bivalent metal element decreases in the content relatively and interferes with preparing the self-molding permanent of the present invention. Preferably, the additive can be added to the molding composition (b) in the range of 0.01~20 weight %.

The molding composition (b) of the present invention can be prepared by mixing each constituent described above in deionized water. The molding composition (b) is adjusted to have the range of pH 2~12 and if the reducing composition is less than pH 2 or over pH 12, the reductive power may be reduced. Preferably, the molding composition (b) is prepared to have the range of pH 5~11.

The molding composition (b) of the present invention comprises in the content ratio as follows: 0.1~25 weight % of bivalent metal (preferably, 1~20 weight %); 0~30 weight % of ordinary additive (preferably, 0.01~20 weight %); and 60~99.9 weight % of deionized water (preferably, 70~98 weight %).

In the molding composition (b) of the present invention, the bivalent metal is added in the range of 0.0001~5 weight parts per 1 weight part of a molding stimulant contained in the reducing composition (a). If the amount of bivalent metal is less than 0.0001 weight part, hair is not molded sufficiently. In contrast, if the amount of bivalent metal is over 5 weight parts, hair is not softened properly in the softening step and the reductive power decreases. Preferably, the bivalent metal is added in the range of 0.001~0.5 weight parts per 1 weight part of a molding stimulant.

Third, the softening composition (c) of the present permanent agent is combined with a softening agent as an essential component to smoothen hair releasing the molding action and remold hair permanently.

The molding product that is formed by reacting the reducing composition (a) with the molding composition (b) is unfolded by breaking a chemical bond. At this moment, pH is adjusted, or ion or compound is added to substitute a bivalent metal of chemical bond. In the present invention, the softening agent unfolding a molding product can be selected from the group consisting of organic acid, inorganic acid, or/and their acid salt and minerals and preferably, organic acid is selected from the group consisting of citric acid, succinic acid and acetic acid; inorganic acid is selected from the group consisting of nitric acid, sulfuric acid, carbonic acid, bicarbonic acid, hydrochloric acid and phosphoric acid; and minerals is selected from the group consisting of yellow earth, illite, quartz porphyry, bentonite and monmorylonite. The acid salt can be selected from the group consisting of alkali metal salt containing sodium ($Na^+$), potassium ($K^+$) and alkali earth metal containing magnesium ($Mg^{2+}$) and calcium ($Ca^{2+}$). The softening agent can be added to the softening composition (c) in the range of 0.1~25 weight %. If the content of softening agent is less than 0.1 weight %, the molding product is not unfold properly and if the content of softening agent is over 25 weight %, hair is injured problematically. Preferably, the softening agent can be added to the softening composition (c) in the range of 1~20 weight %.

In the softening composition (c) of the present invention, an oxidant can be included additionally. The oxidant can be selected from the group consisting of peroxide solution, peroxides such as urea peroxide, bromates such as alkali metal-containing bromate and peroxy salts and used solely or coordinately in a mixture. The oxidant can be added to the softening composition (c) in the range of 0~25 weight %. If the content of oxidant is over 25 weight %, hair is injured problematically. Preferably, the oxidant can be added to the softening composition (c) in the range of 1~20 weight %.

In the softening composition (c) of the present invention, an oxidizing catalyst can be included additionally, which helps the permeation of softening composition on the hair, stimulates the oxidation of disulfide bond dissociated by the reducing composition (a) and induces to remold hair. The oxidizing catalyst can be a metal or a metal compound and preferably, selected from the group consisting of iron, zinc, copper, cobalt, zirconium, vanadium, manganese and titanium and used solely or coordinately in a mixture. Preferably, the oxidizing catalyst is a powder or liquid form of a metal or a metal compound of nano-size to enhance the catalytic activity. More preferably, the oxidizing catalyst can be a metal oxide selected from the group consisting of iron oxide, zinc oxide, copper oxide, cobalt oxide, zirconium oxide, vanadium oxide, manganese oxide and titanium oxide. The oxidizing catalyst can be added to the softening composition (c) in the range of 0~5 weight %. Even if the content of oxidizing catalyst is over 5 weight %, the catalytic activity is not enhanced in the economical respect.

Preferably, the oxidizing catalyst can be added to the softening composition (c) in the range of 0.0001~5 weight %.

In the softening composition for a permanent agent, any treatment agent such as alkalinizing agent, acidifying agent, metal ion blocker, turbidity agent, amino acids, keratin, silicon, wax, polymer, expansion agent, penetration agent, fat alcohol, lanoline derivative, ceramide, glycols, collagen, active component, preventive of hair loss, dandruff preventive agent, suspension agent, coloring agent, sun blocker, conservative and the like can be added solely or coordinately in a mixture. Also, protein, amino acid and the like can be added to give nutrients on the hair and a surface active agent can be added for the function of shampoo and rinse. The additive described above can be an ordinary component for a permanent agent. It is natural that the additive described above can be selected arbitrarily by those skilled in this art. The above-mentioned additive can be added to the softening composition (c) in the range of 0~30 weight %. If the content of additive is used over 30 weight %, the softening agent and an oxidant decrease relatively in the content to interfere the softening action and the oxidation on the hair. Preferably, the additive can be added to the softening composition (c) in the range of 0.01~20 weight %.

The softening composition (c) of the present invention can be prepared by mixing each constituent described above in deionized water. The softening composition (c) is adjusted to have the range of pH 2~9 and if the reducing composition is less than pH 2 or over pH 9, hair may be injured. Preferably, the softening composition (c) is prepared to have the range of pH 3~8.

The softening composition (c) of the present invention comprises in the content ratio as follows: 0.1~25 weight % of softening agent (preferably, 1~20 weight %); 0~25 weight % of oxidant (preferably, 1~20 weight %); 0~5 weight % of reduction catalyst (preferably, 0.0001~5 weight %); 0~30 weight % of ordinary additive (preferably, 0.01~20 weight %); and 50~99.9 weight % of deionized water (preferably, 70~98 weight %).

In the softening composition (c) of the present invention, the softening agent is added in the range of 0.1~50 weight parts (preferably, 1~10 weight parts) per 1 weight part of a molding stimulant. If the amount of softening agent is less than 0.1 weight part, hair is not softened properly. If the amount of softening agent is over 50 weight parts, the softening action is not economical.

The oxidant can be added in the range of 0.1~10 weight parts (preferably, 0.5~2 weight parts) per 1 weight part of softening agent. If the amount of oxidant is less than 0.1 weight parts, the oxidative power decreases. In contrast, if the amount of oxidant is over 10 weight parts, it is disadvantageous to increase the oxidation extremely on the hair and causes an economical loss.

So far, the 3-solution type permanent agent of the present invention comprised of a reducing composition (a), a molding composition (b) and a softening composition (c) is described, aiming to each constituent and its application.

The present invention provides a 4-solution type permanent agent wherein an oxidant is separated from the softening composition (c) mentioned above and an oxidizing composition (d) is prepared. That is to say, the 4-solution type permanent agent of the present invention is comprised of a reducing composition (a), a molding composition (b), a softening composition (c) and an oxidizing composition (d).

In the 4-solution type permanent agent of the present invention, an oxidant is an essential component to prepare the oxidizing composition (d). If necessary, an oxidizing catalyst can be used. The oxidant or both the oxidant and oxidizing catalyst, if necessary, can be used to prepare the softening composition (c).

In the 4-solution type permanent agent of the present invention, the oxidant as an essential component of the oxidizing composition (d) can be selected from the group consisting of peroxide solution, peroxides such as urea peroxide, bromates such as alkali metal-containing bromate and peroxy salts and used solely or coordinately in a mixture. The oxidizing composition (d) can contain an oxidant in the range of 0.1~25 weight %. If the content of oxidant is less than 0.1 weight %, the oxidation is not performed properly. If the content of oxidant is over 25 weight %, hair tends to be injured. Preferably, the oxidizing composition (d) can contain an oxidant in the range of 1~20 weight %.

Preferably, the oxidizing composition (d) can include an oxidizing catalyst selected from the group consisting of iron, zinc, copper, cobalt, zirconium, vanadium, manganese and titanium solely or coordinately, as demonstrated in the softening composition (c). Preferably, the oxidizing catalyst is a powder or liquid form containing a metal or a metal compound of nano-size to enhance the catalytic activity. The oxidizing composition (d) can include the oxidizing catalyst in the range of 0~5 weight %. Even if the content of oxidizing catalyst is over 5 weight %, the catalytic activity is not enhanced in the economical respect. Preferably, the oxidizing composition (d) can include the oxidizing catalyst in the range of 0.0001~5 weight %.

In the oxidizing composition for a permanent agent, any treatment agent such as alkalinizing agent, acidifying agent, metal ion blocker, turbidity agent, amino acids, keratin, silicon, wax, polymer, expansion agent, penetration agent, fat alcohol, lanoline derivative, ceramide, glycols, cellulose system, active component, preventive of hair loss, dandruff preventive agent, suspension agent, coloring agent, sun blocker, conservative and the like can be added solely or coordinately in a mixture. When hydrogen peroxide is used as an oxidant, phenacetin, acetoaniline, mono- and tri-sodium phosphate or 8-hydroxyquinoline sulfate can be added to stabilize the reaction. The additive described above can be an ordinary constituent for a permanent agent. It is natural that the additive described above can be selected arbitrarily by those skilled in this art. The above-mentioned additive can be added to the oxidizing composition (d) of the present invention in the range of 0~30 weight %. If the content of additive is over 30 weight %, the content of oxidant and oxidizing catalyst decreases relatively to reduce the oxidative power. Preferably, the additive can be added to the oxidizing composition (d) of the present invention in the range of 0.01~20 weight %.

The oxidizing composition (d) of the present invention can be prepared by mixing each constituent described above in deionized water. The oxidizing composition (d) is adjusted to have the range of pH 2~7 and if the reducing composition is less than pH 2 or over pH 7, hair wave may not be maintained because the oxidative power is reduced or increased extremely. Preferably, the oxidizing composition (d) is prepared to have the range of pH 3~6.

The oxidizing composition (d) of the present invention comprises in the content ratio as follows: 0.1~25 weight % of oxidant (preferably, 1~20 weight %); 0~5 weight % of oxidizing catalyst (preferably, 0.0001~5 weight %); 0~30 weight % of ordinary additive (preferably, 0.01~20 weight %); and 60~99.9 weight % of deionized water (preferably, 70~98 weight %).

In the 4-solution type permanent agent, the content of oxidant can be in the range of 0.1~10 weight parts (preferably, 0.5~2 weight parts) per 1 weight part of softening agent contained in the softening composition (c), as explained in the 3-solution type permanent agent. If the amount of oxidizing agent is less than 0.1 weight part, the oxidative power decreases. In contrast, if the amount of oxidizing agent is over 10 weight parts, the oxidation is heavily proceeded on the hair in the economical respect.

In the meantime, the present invention provides a method for pressing a free-rod and free-band type permanent, which can apply a semi-permanent wave on the hair without a hair-curling device.

Precisely, the method for pressing a permanent of the present invention (in 3-solution type) can be performed by following steps, which comprises: (1) coating a reducing composition comprising a reducing agent and a molding stimulant on the hair; (2) curling hair coated with the reducing composition; (3) coating a molding composition inducing to mold after reacting with the molding stimulant, on the hair curled above; (4) coating a softening composition on the hair molded above to stop the molding action; and (5) washing hair coated with the softening composition.

In addition, the method for pressing a permanent of the present invention (in 4-solution type) can be performed by following steps, which comprises: (1) coating a reducing composition comprising a reducing agent and a molding stimulant on the hair; (2) curling hair coated with the reducing composition; (3) coating a molding composition inducing to mold after reacting with the molding stimulant, on the hair curled above to mold the hair; (4) coating an oxidizing composition on the hair molded above and then coating a softening composition on the hair oxidized above to stop the molding action; and (5) washing hair coated with the softening composition.

That is to say, in the method for pressing a permanent of the present invention, the process for performing a 3-solution type permanent is a basic procedure, which comprises several essential steps as follows: (1) coating a reducing composition comprising a molding stimulant uniformly on the hair; (2) curling hair in a desired mode by the hand or by a hair setting device; (3) coating a molding composition on the hair, inducing to mold, detaching the hair setting device and maintaining for some time period to mold the hair; (4) coating a softening composition on the hair to stop the molding action; and (5) washing hair.

In order to perform the method for pressing a permanent by using the 3-solution type permanent agent, an oxidant and an oxidizing catalyst can be added selectively. Preferably, both oxidant and oxidizing catalyst can be added to a softening composition.

In the method for pressing a permanent by using the 4-solution type permanent agent, the step coating an oxidizing composition (d) on the hair is prerequisite and accordingly, the step releasing the molding action is needed after coating the oxidizing composition (d) on the hair.

In order to perform the process for pressing a permanent of the present invention, hair can be curled in a desired mode by the hand in the step (b) molding hair, since the reducing composition has some extent of viscosity and adhesiveness. If necessary, a hair-curling device can be used properly and hair curl can be sustained for a time even if detaching a curling device, since the permanent agent of the present invention retains the elasticity and the hardness after coating the molding composition (b).

The reducing composition and the molding composition contained in the permanent agent of the present invention can apply a hair curl in a desired mode even at room temperature without heating. As a reference, hair coated with the reducing composition can be heat-treated at 30~60° C. or after washed off, at 180~200° C. Hair curl can be controlled in the extent selectively by the heat treatment, which minimizes the time period for a permanent press. In practice, such a manipulation is accomplished under hair drying hood, hair drier, infrared ray emitter or ordinary heating apparatus.

In the process for pressing a permanent of the present invention, the time period contacting hair with the permanent agent can be about 1~40 minutes without heating, depending upon a hair state and preferably 2~20 minutes.

As a consequence, the method for pressing a permanent of the present invention is distinguished from a conventional method for pressing a permanent in several respects as follows.

First, any user can design a hair in a desired mode easily even by the hand.

Second, any user can apply a hair wave without a hair-curling device such as perm rod and rubber band.

Third, some protective membrane is formed spontaneously to prevent a permanent agent from drying and separate it from outer environment.

Fourth, the time period for performing a permanent press is short.

EXAMPLES

Practical and presently preferred embodiments of the present invention are illustrated as shown in the following Preparations and Examples.

However, it will be appreciated that those skilled in the art, on consideration of this disclosure, may make modifications and improvements within the spirit and scope of the present invention.

<Preparations> Production of Nano-Sized Metal Catalyst
<Preparation 1> Production of Colloidal-Type Gold Nano-Sized Particles Above all, 10% $HAuCl_4.H_2O$ (1 mL) and water (79 mL) were mixed to prepare solution A. In a separate vessel, 1% of sodium citrate, (4 mL), 1% of tannic acid (0.1 mL) and water (20 mL) were mixed to prepare solution B. While solution A was heated at 60° C., solution B was added rapidly, reacted and then cooled and centrifuged to produce colloidal-type gold nano-sized particle (average radius 10 nm).

<Preparation 2> Production of Colloidal-Type Platinum Nano-Sized Particles $H_2PtCl_6.H_2O$ (1 mL) and water (79 mL) were mixed to prepare solution A. In a separate vessel, 1% of sodium citrate, (4 mL), 1% of tannic acid (0.1 mL) and water (20 mL) were mixed to prepare solution B. While solution A was heated at 60° C., solution B was added rapidly, reacted, and then cooled and centrifuged to produce colloidal-type platinum nano-sized particle (average radius 10 nm).

<Preparation 3> Production of Colloidal-Type Rhodium Nano-Sized Particles

10% $RhCl_3.H_2O$ (1 mL) and water (79 mL) were mixed to prepare solution A. In a separate vessel, 1% of sodium citrate, (4 mL), 1% of tannic acid (0.1 mL) and water (20 mL) were mixed to prepare solution B. While solution A was heated at 60° C., solution B was added rapidly, reacted and then cooled and centrifuged to produce colloidal-type rhodium nano-sized particle (average radius 10 nm).

<Preparation 4> Production of Colloidal-Type Titanium Dioxide Nano-Sized Particles Titanium isopropoxide (1 mL) and ethanol (99 mL) were mixed. Then, 35% of hydrochloric acid solution (2 mL) was added to the mixed solution, stirred and heated at 60° C. and after the reaction, cooled to produce colloidal-type titanium dioxide nano-sized particle (average radius 10 nm).

<Preparation 5> Production of Colloidal-Type Zinc Oxide Nano-Sized Particles

Zinc chloride (1 mL) and ethanol (99 mL) were mixed. Then, 35% of hydrochloric acid solution (2 mL) was added to the mixed solution, stirred and heated at 60° C. and after the reaction, cooled to produce colloidal-type zinc oxide nano-sized particle (average radius 10 nm).

<Preparation 6> Production of Colloidal-Type Vanadium Oxide Nano-Sized Particles Ammonium metavanadate (1 mL) and ethanol (99 mL) were mixed. Then, 35% of hydrochloric acid solution (2 mL) was added to the mixed solution, stirred and heated at 60° C. and after the reaction, cooled to produce colloidal-type vanadium oxide nano-sized particle (average radius 10 nm).

Examples Preparation of Permanent Agent

Example 1

Reducing composition: ammonium thioglycolate (50%) (10.0 g), ammonia water (28%) (3.0 g), sterimonium chloride (0.1 g), propylene glycol (5.0 g), fragrance (0.5 g), algin (3.0 g), 1% gold nano-sized particle solution (average radius 10 nm) (0.1 g), polyvinyl alcohol (0.1 g), pigment (orange 11) (0.1 g), EDTA (0.2 g), and deionized water (77.9 g) were mixed, then ammonium thioglycolate, ammonia or the like were added in the last and adjusted to pH 9.3.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93 g) were mixed homogeneously and adjusted to pH 10.7.

Oxidizing composition: sodium bromate (5.0 g) and deionized water (95 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

The reducing composition was spread on the hair and the hair was designed by using a hair-curling device or by the hand and then, the molding composition was applied on the hair. After that, the hair was detached from the device or the hand and maintained to react with the reducing composition for about 15 minutes. After completing the reduction, the oxidizing composition and the softening composition were added on the hair in order and reacted for about 15 minutes to release the molded hair and complete the oxidation. Then, the hair was washed cleanly and treated with a hair nutrient product to finish a permanent press up.

Through the operation using above-mentioned compositions, the hair can be designed naturally and maintained strongly and elastically since it is not pressed down by a rod weight and does not have a track of rubber band.

Figure 3:
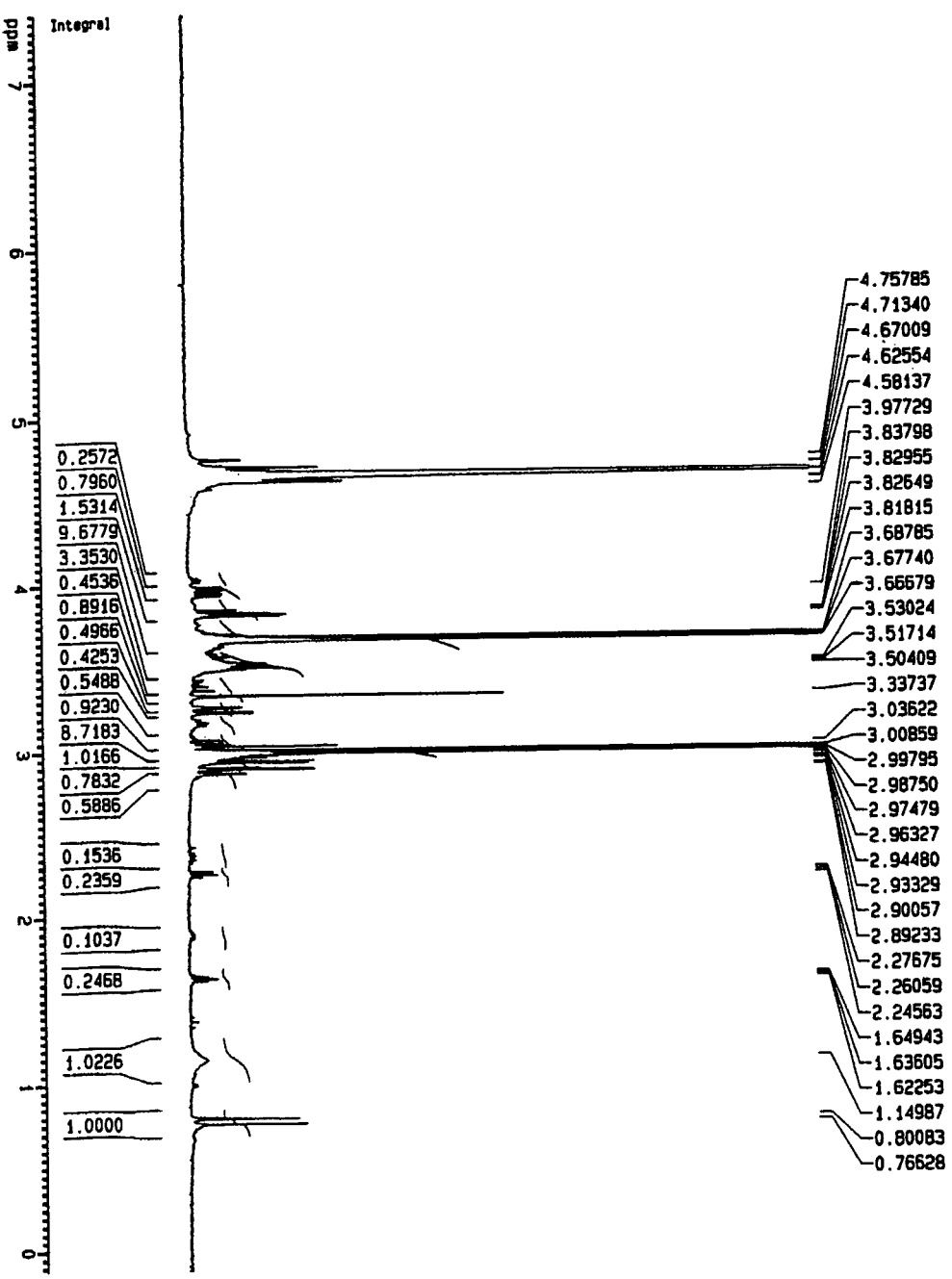
FIG. 3 illustrates $^1$H-NMR (500 MHz) spectroscopic data of the reducing composition prepared in Example 1 of the present invention.

FIG. 3 illustrates $^1$H-NMR (500 MHz) spectroscopic spectrum of the reducing composition (a) prepared in Example 1 and as a result, a peak corresponding to algin was detected near at 65 ppm.

Example 2

Reducing composition: ammonium thioglycolate (50%) (10.0 g), monoethanolaminethioglycol (50%) (0.1 g), ammonia water (28%) (3.0 g), sterimonium chloride (0.1 g), propylene glycol (5.0 g), fragrance (0.5 g), algin (3.0 g), 1% platinum nano-sized particle solution (average radius 10 nm) (0.1 g), pigment (orange II) (0.1 g), EDTA (0.2 g), and deionized water (77.9 g) were mixed, then ammonium thioglycolate, ammonia or the like were added in the last and adjusted to pH 9.3.

Molding composition: monoethanolamine (0.1%), ammonia water (28%) (0.9 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Oxidizing composition: hydrogen peroxide (35%) (5.07 g), phenacetin (1.0 g), and deionized water (95 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% titanium dioxide nano-sized particle (average radius 10 nm) (0.2 g), pigment (orange II) (0.1 g) and deionized water (95.9 g) were mixed homogeneously and adjusted to pH 5.

The permanent agent was prepared by the same procedure described in Example 1 and applied on the hair directly. As a result, the hair was not pressed down by a rod weight and does not have a track of rubber band, but designed naturally and maintained strongly and elastically as if it is made by a general procedure (using rod, rubber band, vinyl cap or the like).

Figure 4:
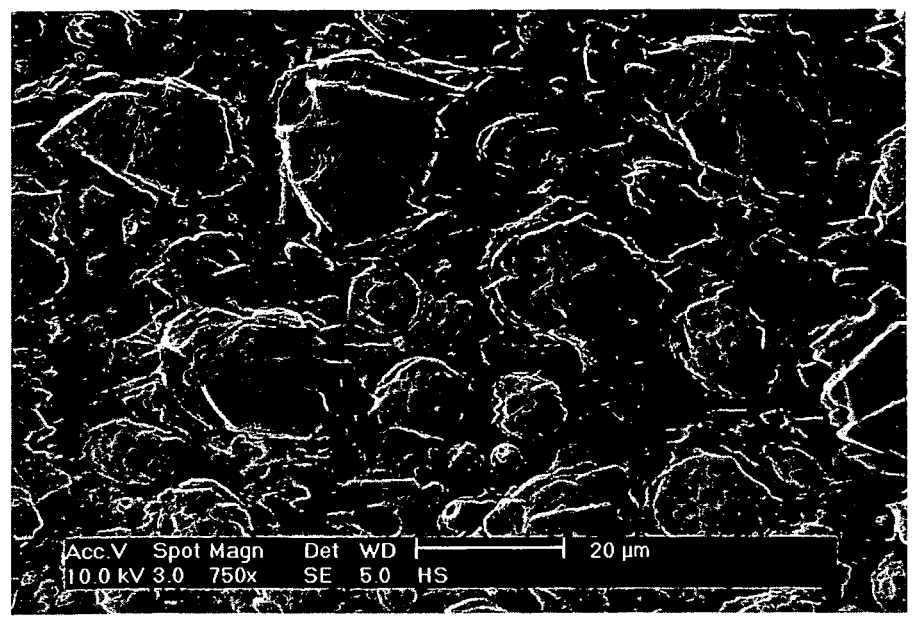
FIG. 4 illustrates scanning electron microscopic (SEM) data of the fragment of plate coated with a mixture after blending the reducing composition and the molding composition prepared in Example 2 of the present invention.

FIG. 4 illustrates the scanning electron microscopic (SEM) data of the plate coated with a mixture after blending the reducing composition and the molding composition prepared in Example and as a result, a network structure was observed on the SEM photograph. It is concluded that oxygen gas, hair nutrient component, reducing agent and the like may be permeated through a pore channel within the network structure to reach the hair.

Example 3

Reducing composition: ammonium thioglycolate (50%) (0.3 g), cysteine hydrochloride (8.0 g), N-acetylcysteine (0.01 g), monoethanolamine (2.0 g), sterimonium chloride (0.1 g), polyethyleneglycol (5.0 g), algin (3.0 g), 1% platinum nano-sized particle solution (average radius 10 nm) (0.1 g), chito acid (purchased from Aldrich; 1% solution, 20~200 cps of viscosity, 0.1 g), fragrance (0.1 g), EDTA (0.2 g), and deionized water (81.09 g) were mixed, and adjusted to pH 9.3.

Molding composition: ammonia water (28%) (1.0 g), fragrance (0.2 g), oleyl alcohol (ethylene oxide 20 M) (0.2 g), calcium chloride (5.0 g), propylene glycol (2.5 g), oxalic acid (0.1 g) and deionized water (91.0 g) were mixed and adjusted to pH 10.7.

Oxidizing composition: sodium bromate (5.0 g) and deionized water (95.0 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% titanium dioxide nano-sized particle (average radius 10 nm) (0.2 g), pigment (orange II) (0.1 g) and deionized water (95.9 g) were mixed homogeneously and adjusted to pH 4.1.

The permanent agent was prepared by the same procedure described in Example 1 and applied on the hair. As a result, the hair curl was sustained strongly and elastically and further, designed naturally since the hair was not pressed down by a rod weight and does not have a track of rubber band.

Example 4

Reducing composition: ammonium thioglycolate (50%) (0.3 g), cysteine free base (5.0 g), monoethanolamine (2.0 g), sterimonium chloride (0.1 g), polyethyleneglycol (5.0 g), algin (3.0 g), 1% platinum nano-sized particle solution (average radius 10 nm) (0.1 g), poly-L-lysine (3.1 g), fragrance (0.1 g), EDTA (0.2 g), and deionized water (81.1 g) were mixed, and adjusted to pH 9.3.

Molding composition: isopropylamine (0.1 g), ammonia water (28%) (0.9 g), fragrance (0.2 g), oleyl alcohol (ethylene oxide 20 M) (0.2 g), barium chloride (5.0 g), propylene glycol (2.5 g), oxalic acid (0.1 g) and deionized water (91.0 g) were mixed and adjusted to pH 10.7.

Oxidizing composition: hydrogen peroxide (35%) (5.07 g), phenacetin (1.0 g) and deionized water (93.93 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% titanium dioxide nano-sized particle (average radius 10 nm) (0.2 g), pigment (orange II) (0.1 g) and deionized water (95.9 g) were mixed homogeneously and adjusted to pH 4.1.

The permanent agent was prepared by the same procedure described in Example 1 and applied on the hair directly. As a result, the hair curl was sustained strongly and elastically and further, designed naturally since the hair was not pressed down by a rod weight and does not have a track of rubber band.

Example 5

Reducing composition: commercial permanent agent 1 (pH 9.3; purchased from Terra Cosmetics CUME; containing cysteine hydrochloride) (91.4 g), algin (2.0 g), 1% platinum nano-sized particle solution (average radius 10 nm) (0.1 g), cellulose acetate (1.5 g) and deionized water (5.0 g) were mixed, and adjusted to pH 9.3.

Molding composition: ammonia water (28%) (1.0 g), fragrance (0.2 g), oleyl alcohol (ethylene oxide 20 M) (0.2 g), strontium chloride (5.0 g), propylene glycol (2.5 g), oxalic acid (0.1 g) and deionized water (91.0 g) were mixed uniformly and adjusted to pH 10.7.

Oxidizing composition: sodium bromate (5.0 g) and deionized water (95.0 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% vanadium oxide nano-sized particle (average radius 10 nm) (0.2 g), pigment (orange II) (0.1 g) and deionized water (95.9 g) were mixed homogeneously and adjusted to pH 4.1.

For a reducing composition, commercially available permanent agent 1 (pH 9.3) was adopted and then, a molding stimulant was added. The same result was obtained as described in Example 1 and Example 2. As a result, it is confirmed that commercial permanent agent 1 can be used instead of a reducing agent.

Example 6

Reducing composition: commercial permanent agent 1 (pH 9.3; purchased from Terra Cosmetics CUME; containing cysteine hydrochloride) (91.3 g), algin (2.0 g), 1% platinum nano-sized particle solution (average radius 10 nm) (0.1 g), butylenes glycol (0.5 g), collagen (1.6 g) and deionized water (5.0 g) were mixed, and adjusted to pH 9.3.

Molding composition: methylethanolamine (0.1 g), ammonia water (28%) (0.9 g), fragrance (0.2 g), oleyl alcohol (ethylene oxide 20 M) (0.2 g), calcium acetate (5.0 g), propylene glycol (2.5 g), oxalic acid (0.1 g) and deionized water (93.0 g) were mixed uniformly and adjusted to pH 10.7.

Oxidizing composition: hydrogen peroxide (35%) (5.07 g), phenacetin (1.0 g) and deionized water (93.93 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described in Example 5 and Example 6, commercial permanent agent 1 (pH 9.3) was adopted and then, a molding stimulant was added to prepare the reducing composition. The same result was obtained as described in Example 1~4. As a result, it is clarified that commercial permanent agent 1 can replace a reducing agent and additives in the reducing composition and combine with other constituents of permanent agent in the present invention to have a good permanent effect.

Example 7

Reducing composition: commercial permanent agent 1 (pH 6.5; purchased from Iljin Cosmetics AROKOS; containing cysteine hydrochloride and ammonium thioglycolate) (86.9 g), algin (3.0 g), 1% gold nano-sized particle solution (average radius 10 nm) (0.1 g), lactone (3.0 g), EDTA (0.1 g) and deionized water (6.9 g) were mixed, and adjusted to pH 9.3.

Molding composition: ammonia water (28%) (0.9 g), fragrance (0.2 g), oleyl alcohol (ethylene oxide 20 M) (0.2 g), calcium nitric acid (5.0 g), propylene glycol (0.5 g), oxalic acid (0.1 g) and deionized water (93.0 g) were mixed uniformly and adjusted to pH 10.7.

Oxidizing composition: sodium bromate (5.0 g) and deionized water (95.0 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

Commercial permanent agent 1 (pH 6.5) was adopted and then, a molding stimulant was added to prepare the reducing composition. The same result was obtained as described in Example 1~ and Example 2. As a result, it is clarified that commercial permanent agent 1 can replace a reducing agent and additives in the reducing composition and combine with other constituents of permanent agent in the present invention to have a good permanent effect.

Example 8

Reducing composition: commercial permanent agent 1 (pH 6.5; purchased from Iljin Cosmetics AROKOS; containing cysteine hydrochloride and ammonium thioglycolate) (86.9 g), algin (3.0 g), 1% platinum nano-sized particle solution (average radius 10 nm) (0.1 g), sodium caseinate (1.0 g), EDTA (0.1 g) and deionized water (8.9 g) were mixed, and adjusted to pH 6.5.

Molding composition: ammonia water (28%) (0.9 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Oxidizing composition: hydrogen peroxide (35%) (5.07 g), phenacetin (1.0 g) and deionized water (93.93 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described in Example 7 and Example 8, commercial permanent agent 1 (pH 6.5) was adopted and then, a molding stimulant was added to prepare the reducing composition. The same result was obtained as described in Example 1~4. As a result, it is clarified that commercial permanent agent 1 can replace a reducing agent and additives in the reducing composition and combine with other constituents of permanent agent in the present invention to have a good permanent effect.

Example 9

Reducing composition: commercial permanent agent 1 (pH 9.6; purchased from Beebongfine SCHIMER; containing thioglycolic acid as a main component) (86.9 g), algin (3.0 g), 1% gold nano-sized particle solution (average radius 10 nm)

(0.1 g), propylene glycol (4.0 g), arginine (1.0 g), EDTA (0.1 g) and deionized water (4.9 g) were mixed, and adjusted to pH 9.6.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Oxidizing composition: sodium bromate (5.0 g) and deionized water 95.0 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% titanium dioxide nano-sized particle (average radius 10 nm) (0.2 g), pigment (orange II) (0.1 g) and deionized water (95.9 g) were mixed homogeneously and adjusted to pH 4.1.

A heater permanent agent 1 (pH 9.6) commercially available was exploited after adding a molding stimulant, coated on the hair, washed and then, a hair wave is fixed and heated at 270° C. The same result was obtained as described in Example 1~2. As a result, it is clarified that commercial permanent agent 1 can replace a reducing agent and additives in the reducing composition and combine with other constituents of permanent agent in the present invention to have a good permanent effect.

Example 10

Reducing composition: commercial permanent agent 1 (pH 9.3; purchased from Beebongfine SCHIMER; containing thioglycolic acid as a main component) (86.9 g), algin (3.0 g), 1% gold nano-sized particle solution (average radius 10 nm) (0.1 g), propylene glycol (4.0 g), adipic acid (1.0 g), EDTA (0.1 g) and deionized water (5.0 g) were mixed, and adjusted to pH 9.6.

Molding composition: ammonia water (28%) (1.0 g), fragrance (0.2 g), oleyl alcohol (ethylene oxide 20 M) (0.2 g), calcium chloride (4.9 g), magnesium chloride (0.1 g), propylene glycol (0.5 g), oxalic acid (0.1 g) and deionized water (93.0 g) were mixed uniformly and adjusted to pH 10.7.

Oxidizing composition: hydrogen peroxide (35%) (5.07 g), phenacetin (1.0 g) and deionized water (93.93 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described in Example 9, a heater permanent agent 1 (pH 9.6) commercially available was exploited after adding a molding stimulant, coated on the hair, washed and then, a hair wave is fixed and heated at 200° C. The same result was obtained as described in Example 1~4. As a result, it is clarified that commercial permanent agent 1 can replace a reducing agent and additives of the reducing composition and combine with other constituents of permanent agent in the present invention to have a good permanent effect.

Example 11

Reducing composition: commercial permanent agent 1 (pH 9.6; purchased from Academy EVESCHE; containing cysteine hydrochloride and thioglycolic acid as a main component) (82.1 g), algin (3.0 g), 1% gold nano-sized particle solution (average radius 10 nm) (0.1 g), propylene glycol (4.0 g), gluconic acid (1.0 g), stabilizer (4.9 g) and deionized water (4.9 g) were mixed, and adjusted to pH 9.6.

Molding composition: ammonia water (28%) (1.0 g), fragrance (0.2 g), oleyl alcohol (ethylene oxide 20 M) (0.2 g), calcium chloride (4.9 g), propylene glycol (0.5 g), oxalic acid (0.1 g) and deionized water (93.0 g) were mixed uniformly and adjusted to pH 10.7.

Oxidizing composition: sodium bromate (5.0 g) and deionized water (93.03 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

A heater permanent agent 1 (pH 9.6) commercially available was exploited after adding a molding stimulant, coated on the hair, washed and then, a hair wave is fixed and heated at 200° C. The same result was obtained as described in Example 1~2. As a result, it is clarified that commercial permanent agent 1 can replace a reducing agent and additives of the reducing composition and combine with other constituents of permanent agent in the present invention to have a good permanent effect.

Example 12

Reducing composition: commercial permanent agent 1 (pH 9.3; purchased from Academy EVESCHE; containing cysteine hydrochloride and thioglycolic acid as a main component) (82.1 g), algin (3.0 g), 1% platinum nano-sized particle solution (average radius 10 nm) (0.1 g), propylene glycol (4.0 g), glutaraldehyde (1.0 g), stabilizer (4.9 g) and deionized water (4.9 g) were mixed, and adjusted to pH 9.6.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Oxidizing composition: hydrogen peroxide (35%) (5.07 g), phenacetin 1.0 g) and deionized water (93.03 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described in Example 11, a heater permanent agent 1 (pH 9.6) commercially available was exploited after adding a molding stimulant, coated on the hair, washed and then, a hair wave is fixed and heated at 200° C. The same result was obtained as described in Example 1~4. As a result, it is clarified that commercial permanent agent 1 can replace a reducing agent and additives of the reducing composition and combine with other constituents of permanent agent in the present invention to have a good permanent effect.

Example 13

Reducing composition: commercial permanent agent 1 (pH 6.5; purchased from Iljin Cosmetics AROCOS; containing cysteamine and ammonium thioglycolate) (86.9 g), algin (3.0 g), 1% gold nano-sized particle solution (average radius 10 nm) (0.1 g), butylene glycol (3.0 g), starch (2.0 g), EDTA (0.1 g) and deionized water (5.0 g) were mixed, and adjusted to pH 6.5.

Molding composition: ammonia water (28%) (1.0 g), fragrance (0.2 g), oleyl alcohol (ethylene oxide 20 M) (0.2 g), calcium chloride (4.9 g), propylene glycol (0.5 g), oxalic acid (0.1 g) and deionized water (93.0 g) were mixed uniformly and adjusted to pH 10.7.

Oxidizing composition: sodium bromate (5.0 g) and deionized water (93.03 g) were mixed uniformly.

Softening composition: citric acid (2.0 g), sodium citrate (3.0 g), bentonite (3.0 g), quartz porphyry (3.0 g), sodium carbonate (1.0 g) and deionized water (88.0 g) were mixed homogeneously and adjusted to pH 4.1.

As described in Example 1 and 2, the same result was obtained. As a result, it is clarified that commercial permanent agent 1 can replace a reducing agent and additives of the reducing composition and combine with other constituents of permanent agent in the present invention to have a good permanent effect.

Example 14

Reducing composition: commercial permanent agent 1 (pH 9.3; purchased from Iljin Cosmetics AROCOS; containing cysteamine and ammonium thioglycolate) (86.9 g), algin (3.0 g), 1% platinum nano-sized particle solution (average radius 10 nm) (0.1 g), butylene glycol (5.0 g), EDTA (0.1 g) and deionized water (5.0 g) were mixed, and adjusted to pH 6.5.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g): were mixed uniformly and adjusted to pH 10.7.

Oxidizing composition: hydrogen peroxide (35%) (5.07 g), phenacetin (1.0 g) and deionized water (93.03 g) were mixed uniformly.

Softening composition: citric acid (2.0 g), sodium citrate (3.0 g), bentonite (3.0 g), quartz porphyry (3.0 g), sodium carbonate (1.0 g) and deionized water (88.0 g) were mixed homogeneously and adjusted to pH 4.1.

As described in Example 1~4, the same result was obtained as described in Example 1~4. As a result, it is clarified that commercial permanent agent 1 can replace a reducing agent and additives of the reducing composition and combine with other constituents of permanent agent in the present invention to have a good permanent effect.

Example 15

Reducing composition: potassium thiocyanate (0.5 g), monoethanolamine (proper amount), glycerin (3.0 g), 1% gold nano-sized particle solution (average radius 10 nm) (0.1 g), propylene glycol (1.0 g), algin (3.0 g), gum (1.5 g), ethanol (3.0 g) and deionized water (87.9 g) were mixed, and adjusted to pH 9.7.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described above, potassium thiocyanate that is known to reduce and oxidize in turn, was adopted as a reducing agent in the reducing composition to prepare the 3-solution type permanent agent. The same result was obtained with the 4-solution type permanent agent as described in Example 1~2. As a result, it is clarified that the 3-solution type permanent agent excluding an oxidizing composition should be also effective for pressing a permanent.

Example 16

Reducing composition: sodium sulfite (2.0 g), monoethanolamine (proper mount), glycerin (3.0 g), 1% gold nano-sized particle solution (average radius 10 nm) (0.1 g), propylene glycol (2.5 g), algin (3.0 g), ethanol (3.0 g) and deionized water (86.4 g) were mixed, and adjusted to pH 9.0.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described in Example 15, sodium sulfite known to reduce and oxidize in turn, was adopted as a reducing agent in the reducing composition to prepare the 3-solution type permanent agent. The same result was obtained with that of the 4-solution type permanent agent as described in Example 1~4. As a result, it is clarified that the 3-solution type permanent agent excluding an oxidizing composition should be effective for pressing a permanent.

Example 17

Reducing composition: commercial permanent agent (pH 9.75; Kolmar Korea HAYANBI; containing monoethanolamine glycolate as a main component) (96.7 g), 1% gold nano-sized particle solution (average radius 10 nm) (0.1 g), propylene glycol (1.0 g), algin (3.0 g), and EDTA (0.1 g) were mixed, and adjusted to pH 9.75.

Molding composition: ammonia water (28%) (1.0 g), fragrance (0.2 g), oleyl alcohol (ethylene oxide 20 M) (0.2 g), calcium chloride (5.0 g), butylene glycol (0.5 g), oxalic acid (0.1 g) and deionized water (93.0 g) were mixed uniformly and adjusted to pH 10.7.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described above, commercial permanent agent 1 known to reduce and oxidize in turn, was utilized after adding a molding stimulant. The same result was obtained as described in Example 1~4. As a result, it is clarified that only commercial permanent agent should be effective sufficiently for pressing a permanent, even though excluding an oxidizing composition.

Example 18

Reducing composition: ammonium thioglycolate (50%) (10.0 g), ammonia water (28%) (3.0 g), sterimonium chloride (0.1 g), propylene glycol (4.0 g), fragrance (0.5 g), algin (3.0 g), pectin (1.0 g), polyvinyl alcohol (0.1 g), pigment (orange II) (0.1 g), EDTA (0.2 g) and deionized water (87.9 g) were mixed. At this moment, ammonium thioglycolate and ammonia and the like were added in the last and adjusted to pH 9.3.

Molding composition: ammonia water (28%) (1.0 g), fragrance (0.2 g), oleyl alcohol (ethylene oxide 20 M) (0.2 g), zinc nitrate (5.0 g), DL-cysteine hydrohydrochloride (0.05 g), monoethanolamine thioglycolate (0.05 g), propylene glycol (0.5 g), oxalic acid (0.1 g) and deionized water (92.9 g) were mixed uniformly and adjusted to pH 9.8.

Oxidizing agent: hydrogen peroxide (35%) (5.07 g), phenacetin (1.0 g) and deionized water (93.03 g) were mixed uniformly.

Softening composition: silicon emulsion (1.0 g), sodium phosphate (0.3 g), potassium phosphate (0.4 g), hydrolyzed keratin (0.1 g), citric, acid (1.0 g), sodium citrate (1.0 g), 1% titanium oxide nano-sized particle (average radius 10 nm) (0.2 g), pigment (orange II) (0.1 g) and deionized water (95.9 g) were mixed homogeneously and adjusted to pH 4.1.

As described above, in order to increase the reductive power of molding composition, cysteine and thioglycolic acid salt were added in a small amount and clarified to enhance the reduction.

Example 19

Reducing composition: ammonium thioglycolate (50%) (1.5 g), monoethanolamine thioglycolate (50%) (0.5 g), cysteine hydrochloride (8.5 g), monoethanolamine (8.5 g), polyethyleneglycol (0.5 g), algin (2.0 g), hydrolyzed keratin (0.5 g), collagen (0.5 g), propylene glycol (1.0 g), hexadicamol (2.0 g), stearic acid (0.5 g), glycerin (1.0 g), EDTA (0.4 g), cetylammonium chloride (1.0 g), sorbitan (1.5 g), squalene (0.1 g) and deionized water (70.0 g) were mixed and adjusted to pH 9.3.

Molding composition: glycerin (1.0 g), calcium lactate (2.0 g), calcium acetate (1.0 g), hydrolyzed keratin (0.5 g), collagen (0.5 g) and deionized water (94.5 g) were mixed and adjusted to pH 8.5.

Oxidizing agent: hydrogen peroxide (38%) (5.0 g), phenacetin (0.1 g), citric acid (0.5 g) and deionized water (94.4 g) were mixed uniformly.

Softening composition: silicon emulsion (1.0 g), hydrolyzed keratin (0.2 g), citric acid (0.5 g), sodium citrate (2.0 g), potassium citrate (0.5 g), 1% titanium oxide nano-sized particle (average radius 10 nm) (0.1 g) and deionized water (95.7 g) were mixed homogeneously and adjusted to pH 5.0.

As a result, the molding action and the oxidation can be accomplished easily, because inorganic acid salt and a small amount of catalyst were added to the softening composition as described above.

Example 20

Reducing composition: ammonium thioglycolate (50%) (10.0 g), ammonia water (28%) (3.0 g), sterimonium chloride (0.1 g), propylene glycol (5.0 g), fragrance (0.5 g), algin (3.0 g), 1% rhodium nano-sized particle solution (average radius 10 nm) (0.1 g), polyvinyl alcohol (0.1 g), pigment (orange II) (0.1 g), EDTA (0.2 g) and deionized water (77.9 g) were mixed. At this moment, ammonium thioglycolate and ammonia and the like were added in the last and adjusted to pH 9.3.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Oxidizing agent: sodium bromate (5.0 g) and deionized water (95.0 g) were mixed uniformly.

Softening composition: silicon emulsion (1.0 g), sodium phosphate (0.3 g), potassium phosphate (0.4 g), hydrolyzed keratin (0.1 g), citric acid (1.0 g), ammonium chloride (1.0 g), titanium dioxide (0.001 g), 1% titanium oxide nano-sized particle (average radius 10 nm) (0.2 g), pigment (orange II) (0.1 g) and deionized water (95.899 g) were mixed homogeneously and adjusted to pH 4.1.

As a result, the molding action and the oxidation can be accomplished easily, because inorganic acid salt and a small amount of catalyst were added to the softening composition as described above.

Example 21

Reducing composition: ammonium thioglycolate (50%) (10.0 g), ammonia water (28%) (3.0 g), sterimonium chloride (0.1 g), propylene glycol (4.0 g), fragrance (0.5 g), algin (3.0 g), 1% gold nano-sized particle solution (average radius 10 nm) (0.1 g), polyvinyl alcohol (0.1 g), pigment (orange II) (0.1 g), EDTA (0.2 g) and deionized water (77.9 g) were mixed. At this moment, ammonium thioglycolate and ammonia and the like were added in the last and adjusted to pH 9.3.

Molding composition: monoethanolamine (2.0 g), fragrance (0.2 g), oleyl alcohol (ethylene oxide 20 M) (0.2 g), calcium chloride (5.0 g), propylene glycol (0.5 g), oxalic acid (0.1 g) and deionized water (92.0 g) were mixed uniformly and adjusted to pH 10.0.

Oxidizing agent: sodium bromate (5.0 g), titanium dioxide (0.001 g) and deionized water (94.999 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% zinc oxide nano-sized particle (average radius 10 nm) (0.2 g), pigment (orange II) (0.1 g) and deionized water (95.9 g) were mixed homogeneously and adjusted to pH 4.1.

As described above, it is clarified that the oxidative power should be enhanced by adding an oxidizing catalyst to the oxidizing composition.

Example 22

Reducing composition: ammonium thioglycolate (50%) (10.0 g), monoethanolamine (9.0 g), nonionic surface-active agent (3.0 g), collagen (2.0 g), EDTA (0.2 g), cocamidopropyl betaine (1.0 g), fragrance (0.5 g), algin (1.0 g), butylene glycol (0.1 g), pigment (orange II) (0.1 g) and deionized water (75.1 g) were mixed. At this moment, ammonium thioglycolate and ammonia and the like were added in the last and adjusted to pH 9.6.

Molding composition: ammonia water (28%) (1.0 g), fragrance (0.2 g), oleyl alcohol (ethylene oxide 20 M) (0.2 g), calcium chloride (5.0 g), propylene glycol (0.5 g), oxalic acid (0.1 g) and deionized water (93.0 g) were mixed uniformly and adjusted to pH 10.7.

Oxidizing agent: sodium bromate (5.0 g), titanium dioxide (0.001 g) and deionized water (95.0 g) were mixed uniformly.

Softening composition: silicon emulsion (1.0 g), sodium phosphate (0.3 g), potassium phosphate (0.4 g), hydrolyzed keratin (0.1 g), citric acid (1.0 g), sodium citrate (1.0 g), 1% titanium oxide nano-sized particle (average radius 10 nm) (0.2 g), pigment (orange II) (0.1 g) and deionized water (95.9 g) were mixed homogeneously and adjusted to pH 4.1.

As a result, the reducing composition including ammonium thioglycolate, monoethanolamine or the like as a main component can increase the reductive power so that it can be applied for the hair hard to be reduced or for a straight permanent agent.

Example 23

Reducing composition: ammonium thioglycolate (50%) (10.0 g), cysteine hydrochloride (8.0 g), N-acetyl cysteine (1.0 g), sodium sulfite (5.0 g), ammonia water (28%) (4.0 g), monoethanolamine (2.0 g), sodium hydrogen (2.0 g), chito acid (1.0 g), cocamidopropyl betaine (0.5 g), butylenes glycol (2.0 g), propylene glycol (3.0 g), fragrance (0.5 g), algin (2.0 g), 1% gold nano-sized particle solution (average radius 10 nm) (0.6 g), polyvinyl alcohol (0.2 g), pigment (orange II) (0.1 g), EDTA (0.1 g) and deionized water (58.0 g) were mixed. At this moment, ammonium thioglycolate and ammonia and the like were added in the last and adjusted to pH 9.5.

Molding composition: calcium chloride (1.0 g) and deionized water (99.0 g) were mixed and adjusted to pH 10.7.

Softening composition: hydrolyzed keratin (0.5 g), citric acid (2.0 g), calcium citric acid (1.0 g), 1% titanium oxide nano-sized particle (average radius 10 nm) (0.2 g), sodium carbonate (0.5 g), sodium bromate (22.0 g), ceramide (3.0 g), propylene glycol (2.5 g), pigment (orange II) (0.1 g) and deionized water (68.0 g) were mixed homogeneously and adjusted to pH 4.3.

As a result, it is clarified that the oxidative power is enhanced in the softening composition by adding an oxidant.

Example 24

Reducing composition: N-tetramethyl mercaptoacetamide (12.0 g), ammonium hydrogen carbonate (2.0 g), ammonia water (28%) (0.4 g), fragrance (0.5 g), algin (1.0 g), 1% rhodium nano-sized particle solution (average radius 10 nm) (0.1 g), EDTA (0.1 g) and deionized water (75.1 g) were mixed. At this moment, ammonia was added in the last and adjusted to pH 9.3.

Molding composition: calcium acetate (2.5 g), calcium sulfate (7.5 g), magnesium chloride (11.5 g), ammonia water (28%) (0.5 g), oleyl alcohol (3.0 g), oxalic acid (0.5 g) and deionized water (74.5 g) were mixed and adjusted to pH 9.5.

Softening composition: sodium phosphate (2.0 g), potassium phosphate (1.0 g), citric acid (1.0 g), sodium citrate (2.0 g), potassium citrate (5.0 g), 1% iron oxide nano-sized particle (average radius 10 nm) (0.5 g), bentonite (3.0 g), quartz porphyry (2.5 g), sodium carbonate (3.5 g), sodium bromate (1.0 g) and deionized water (95.9 g) were mixed homogeneously and adjusted to pH 4.5.

Example 25

Reducing composition: ammonium thioglycolate (50%) (12.0 g), cysteine hydrochloride (1.0 g), sodium bisulfite (0.5 g), ammonia water (28%) (1.0 g), monoethanolamine (3.0 g), glycerin (2.0 g), propylene glycol (3.0 g), collagen (1.0 g), fragrance (0.5 g), arginine (0.5 g), algin (3.0 g), 1% gold nano-sized particle solution (average radius 10 nm) (3.1 g), pigment (orange II) (0.1 g), EDTA (0.1 g) and deionized water (68.9 g) were mixed. At this moment, ammonium thioglycolate and ammonia and the like were added in the last and adjusted to pH 9.5.

Molding composition: calcium chloride (2.5 g), ammonia water (28%) (1.0 g), DL-cysteine hydrochloride (3.0 g), monoethanolamine thioglycolate (2.0 g), isopropylamine (0.5 g), monoethanolamine (0.5 g), methylethanolamine (0.1 g), oleyl alcohol (2.0 g), propylene glycol (10.0 g), butylene glycol (4.5 g), glycerin (2.0 g), hydrolyzed keratin (5.0 g), collagen (2.0 g), oxalic acid (0.4 g), fragrance (0.5 g) and deionized water (62.0 g) were mixed and adjusted to pH 11.0.

Softening composition: silicon emulsion (2.0 g), sodium phosphate (1.0 g), hydrolyzed keratin (0.5 g), sodium citrate (2.0 g), potassium citrate (2.0 g), 1% titanium oxide nano-sized particle (average radius 10 nm) (4.5 g), 1% vanadium nano-sized particle (average radius 10 nm) (0.5 g), sodium carbonate (2.5 g), quartz porphyry (0.5 g), bentonite (3.0 g), sodium bromate (0.5 g), ceramide (3.0 g), glycerin (3.0 g), propylene glycol (10.0 g), collagen (5.0 g) and deionized water (64.0 g) were mixed homogeneously and adjusted to pH 4.8.

Example 26

Reducing composition: ammonium thioglycolate (50%) (8.0 g), adipic acid (5.3 g), monoethanolamine (3.5 g), non-ionic surface-active agent (4.5 g), polyethylene glycol (7.0 g), sorbitan (2.5 g), squalene (4.7 g), glycerin (8.5 g), ethanol (5.8 g), butylene glycol (6.0 g), propylene glycol (22.0 g), collagen (3.0 g), fragrance (0.5 g), algin (11.0 g), 1% platinum nano-sized particle solution (average radius 10 nm) (0.1 g), pigment (orange II) (0.1 g) and deionized water (75.1 g) were mixed. At this moment, ammonium thioglycolate and ammonia and the like were added in the last and adjusted to pH 10.5.

Molding composition: zinc nitrate (0.5 g), calcium sulfate (2.5 g), strontium chloride (1.5 g), ammonia water (28%) (1.5 g), DL-cysteine hydrochloride (2.0 g), monoethanolamine (0.5 g), oleyl alcohol (2.5 g), propylene glycol (5.0 g), collagen (1.5 g), oxalic acid (0.1 g), fragrance (0.1 g) and deionized water (81.7 g) were mixed and adjusted to pH 10.0.

Oxidizing agent: sodium bromate (22.0 g), titanium dioxide (4.0 g), ceramide (8.9 g), phenacetin (0.1 g) and deionized water (65.0 g) were mixed uniformly.

Softening composition: silicon emulsion (2.5 g), sodium phosphate (1.0 g), hydrolyzed keratin (0.8 g), sodium citrate (3.0 g), potassium citrate (1.0 g), 1% titanium oxide nano-sized particle (average radius 10 nm) (0.5 g), sodium carbonate (2.5 g), quartz porphyry (1.5 g), bentonite (3.0 g), sodium bromate (8.0 g), ceramide (1.0 g), propylene glycol (1.5 g), pigment (orange II) (0.2 g) and deionized water (84.5 g) were mixed homogeneously and adjusted to pH 4.8.

Example 27

Reducing composition: ammonium thioglycolate (50%) (8.0 g), cysteine hydrochloride (1.0 g), ammonia water (28%) (1.0 g), monoethanolamine (2.0 g), sodium laurylsulfite (3.0 g), cocamidopropyl betaine (0.5 g), sorbitan (0.5 g), pectin (0.5 g), glutaraldehyde (0.5 g), poly-L-lysine (0.3 g), arginine (0.7 g), commercial permanent agent 1 (pH 6.5; Iljin Cosmetics AROKOS; containing cysteine hydrochloride and ammonium thioglycolate) (18.0 g)) and deionized water (56.5 g) were mixed. At this moment, ammonium thioglycolate and ammonia and the like were added in the last and adjusted to pH 9.8.

Molding composition: calcium acetate (6.0 g), calcium nitric acid (3.0 g), calcium lactate (1.5 g), ammonia water (28%) (0.5 g), monoethanolamine thioglycolate (1.5 g), methylethanolamine (0.1 g), oleyl alcohol (4.0 g), propylene glycol (0.5 g), butylenes glycol (0.4 g), hydrolyzed keratin (2.0 g), collagen (1.0 g), oxalic acid (0.2 g), fragrance (0.3 g) and deionized water (79.5 g) were mixed and adjusted to pH 10.5.

Softening composition: silicon emulsion (0.5 g), potassium phosphate (0.5 g), hydrolyzed keratin (0.5 g), citric acid (1.5 g), sodium citrate (2.0 g), 1% titanium oxide nano-sized particle (average radius 10 nm) (2.0 g), bentonite (3.0 g), sodium bromate (8.0 g), ceramide (3.5 g), glycerin (2.0 g), pigment (orange II) (0.2 g) and deionized water (78.3 g) were mixed homogeneously and adjusted to pH 3.8.

Example 28

Reducing composition: algin (0.5 g), 1% gold nano-sized particle solution (average radius 10 nm) (0.5 g), commercial permanent agent 1 (pH 9.3; Terra Cosmetics CUME; containing cysteine hydrochloride) (98.0 g) and deionized water (1.0 g) were mixed and adjusted to pH 9.4.

Molding composition: zinc nitrate (2.0 g), calcium nitric acid (1.0 g), isopropylamine (0.5 g), propylene glycol (3.0 g), butylene glycol (1.0 g), glycerin (0.5 g) and deionized water (93.0 g) were mixed and adjusted to pH 8.0.

Oxidizing agent: hydrogen peroxide (35%) (8.0 g), titanium dioxide (0.5 g), ceramide (3.5 g), silicon emulsion (3.0 g), glycerin (10.0 g), hydrolyzed keratin (5.0 g), polyquaternium-10 (2.0 g) and deionized water (71.0 g) were mixed uniformly.

Softening composition: silicon emulsion (1.5 g), sodium phosphate (0.5 g), potassium phosphate (1.5 g), hydrolyzed keratin (0.5 g), citric acid (2.0 g), potassium citrate (0.5 g), 1% titanium oxide nano-sized particle (average radius 10 nm) (2.0 g), sodium carbonate 92.5 g) and deionized water (89.0 g) were mixed homogeneously and adjusted to pH 3.8.

As described above, the permanent agent of the present invention can be used to design a hair while twisting a hair by the hand or applying a wave by the hand or by using a comb, without any other curling device. Besides, the reducing composition can mold the hair in an intended mode spontaneously, even if a hair-curling device is detached after applying a wave set by the device on the hair coated with the composition.

Furthermore, the permanent agent of the present invention can design a hair without a perm rod or band. Precisely, it enables the hair appear abundant, when a hair and scalp are stood perpendicularly for a time period to be molded and can spread a wave, when a hair is pulled out by using a supporting device or a comb.

That is to say, in the processes for pressing a permanent of the present invention, rubber band is not applied or a hair is not designed while wearing a curling device at any time. Therefore, users feel comfortable during the operation.

Experimental Example

Evaluation of Physical Properties of the Permanent Agent

In order to evaluate the physical property of permanent agent prepared in Example 1~28, hair was curled by the procedure as follows. Precisely, a hair bundle that is composed of 30 pieces of intact hairs having 20 cm of length and 15 g of weight was soaked in the reducing composition for 2 minutes, then winded around a rod having 14 mm of radius and sprayed by using 3 mL of the molding composition. After 10 minutes, the hair bundle is sprayed again for 10 minutes by using 3 mL of the oxidizing composition, repeated twice, washed and dried in the air to be curled.

The evaluation data of each test item were summarized in Table 1 as follows. The data depicted in Table 1 were symbolized according to following criteria.

(1) The strength of hair curl
⊚: under 20 mm of radius in a hair curl
O: over 20 mm and under 25 mm of radius in a hair curl
△: over 25 mm and under 30 mm of radius in a hair curl
X: over 30 mm of radius in a hair curl (2) The uniformity of hair curl
⊚: under 4 mm of radius error in each hair curl at the start or at the last
O: under 8 mm and over 4 mm of radius error in each hair curl at the start or at the last
△: under 12 mm and over 8 mm of radius error in each hair curl at the start or at the last
X: over 8 mm of radius error in each hair curl at the start or at the last (3) Estimation of volume sense, glossiness, healthiness and humidity
20 of hair designers have evaluated the volume sense, the glossiness, the healthiness and the humidity of hairs.
⊚: over 15 persons judging to be outstanding
O: over 10 persons and under 15 persons judging to be outstanding
△: over 5 persons and under 10 persons judging to be outstanding
X: under 5 persons judging to be outstanding

TABLE 1

| Items | Physical properties ||||||
|---|---|---|---|---|---|---|
| | Strength | Uniformity | volume | Glossiness | Healthness | humidity |
| Example 1 | ⊚ | ⊚ | ⊚ | ⊚ | ○ | ○ |
| Example 2 | ⊚ | ○ | ⊚ | ○ | △ | △ |
| Example 3 | ○ | ⊚ | ○ | △ | ⊚ | ○ |
| Example 4 | ⊚ | △ | ⊚ | ○ | ○ | ○ |
| Example 5 | ⊚ | ⊚ | ⊚ | ○ | △ | △ |
| Example 6 | ○ | △ | ○ | ○ | △ | △ |
| Example 7 | ○ | ⊚ | ○ | ⊚ | ○ | △ |
| Example 8 | ⊚ | △ | ⊚ | ○ | ○ | ○ |
| Example 9 | ○ | ○ | ○ | △ | ⊚ | ⊚ |
| Example 10 | ⊚ | ⊚ | ⊚ | ○ | △ | △ |
| Example 11 | ⊚ | ⊚ | ○ | ○ | ○ | ○ |
| Example 12 | ⊚ | △ | ⊚ | ⊚ | △ | ⊚ |
| Example 13 | ⊚ | ⊚ | ⊚ | ○ | △ | ○ |
| Example 14 | ○ | ⊚ | ○ | ○ | ○ | △ |
| Example 15 | ○ | ⊚ | ○ | △ | ○ | ○ |
| Example 16 | ⊚ | △ | ⊚ | ○ | △ | △ |
| Example 17 | ⊚ | ○ | ⊚ | ○ | ○ | △ |
| Example 18 | ⊚ | ⊚ | ○ | ○ | ○ | △ |
| Example 19 | ⊚ | ⊚ | ⊚ | △ | ○ | ○ |
| Example 20 | ○ | △ | ○ | ⊚ | ⊚ | ⊚ |
| Example 21 | ⊚ | ⊚ | ○ | △ | ○ | ○ |
| Example 22 | ⊚ | △ | ○ | ⊚ | ○ | ○ |
| Example 23 | ○ | △ | ○ | △ | △ | △ |
| Example 24 | ⊚ | ○ | ○ | △ | ○ | ○ |
| Example 25 | ○ | △ | △ | △ | △ | △ |
| Example 26 | ⊚ | ○ | ○ | △ | △ | ○ |
| Example 27 | ○ | ○ | ○ | △ | ○ | ○ |
| Example 28 | ⊚ | △ | ○ | ○ | ○ | △ |

INDUSTRIAL APPLICABILITY

As illustrated and confirmed above, the present invention relates to a novel self-molding permanent agent and a method for proceeding free-rod and free-band type permanent, which overcomes a disadvantage in the conventional method for performing a permanent that needs to wear a curling device such as perm rod or rubber band.

Precisely, the molding stimulant contained in the permanent agent of the present invention can be applied for a commercial permanent agent such as acidic permanent agent, alkaline permanent agent, permanent agent excluding a neutralizing step, permanent agent for a heating device, permanent agent for setting and straightening agent to have the same effect on any hair-remolding process. The permanent agent of the present invention is identified to apply a wave set strongly and elastically on the hair.

The molding stimulant of permanent agent in the present invention is stable, combined with other constituent providing nutrients on the hair and prepares any other composition modulating the ratio of constituents to satisfy the user's need.

In the process for pressing a permanent of the present invention, a hair-curling device such as perm rod or rubber band is not used consistently at any time. Therefore, the user feels comfortable during the operation and the operator manipulates the permanent press easily.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A kit for a self-molding permanent comprising three compositions:
   (a) a reducing composition containing a reducing agent, a molding stimulant, and a reduction catalyst comprised of a colloidal-type metal or metal compound having nano-sized particles, wherein the colloidal-type metal or the metal compound is selected from the group consisting of gold, platinum, palladium, rhodium, titanium dioxide, zinc oxide, and vanadium oxide;
   (b) a molding composition comprising at least one bivalent metal or metal compound and its soluble salt to form a molding membrane with the molding stimulant in the reducing composition (a), wherein the at least one bivalent metal or metal compound is present in an amount from 0.001 to 5 weight parts per 1 weight part of the molding stimulant contained in the reducing composition (a); and
   (c) a softening composition releasing the action of the molding stimulant.

2. The kit for a self-molding permanent according to claim 1, further comprising a fourth composition:
   (d) an oxidizing composition containing an oxidant.

3. The kit for a self-molding permanent according to claim 1 or claim 2, wherein the reducing composition (a) has a pH in the range of 4~11.

4. The kit for a self-molding permanent according to claim 1 or claim 2, wherein the reducing composition (a) further contains a reducing agent having a functional group selected from the group consisting of sulfide, bisulfide, thiol, cyanide, thiocyanide, hydroxide, sulfite, bisulfite and bicarbonate.

5. The kit for a self-molding permanent according to claim 4, wherein the reducing agent is selected from the group consisting of thioglycolic acid or its salt, thioglycolic acid ester, thiolactic acid, thiolactic acid ester, cysteine, cysteamine, thiocyanide, sulfite and their derivatives.

6. The kit for a self-molding permanent according to claim 1, wherein the molding stimulant is selected from the group consisting of algin, alginic acid, alginate, alginic acid salt and their derivatives.

7. The kit for a self-molding permanent according to claim 6, wherein the derivatives have at least one functional group selected from the group consisting of univalent or multivalent hydroxyl group, aldehyde, carboxylic acid, carboxylate and ketone.

8. The kit for a self-molding permanent according to claim 1 or claim 2, wherein the reducing composition (a) contains a reducing agent and a molding stimulant in a 1:0.01~1 of weight ratio.

9. The kit for a self-molding permanent according to claim 1 or claim 2, wherein the reducing composition (a) has the viscosity in the range of 6,000~60,000 cP.

10. The kit for a self-molding permanent according to claim 1 or claim 2, wherein the reducing composition (a) contains a reactive substance having a reactive group that is selected from the group consisting of hydroxyl (—OH), carboxylic acid (—COOH), ketone (—CO), carboxylate (—COOR) and aldehyde (—COH).

11. The kit for a self-molding permanent according to claim 10, wherein the reactive substance is selected from the group consisting of glycol, polyalkylene glycol, polyols containing polyvinyl alcohol, chitin or its derivatives, chito acid or its derivatives, maleic acid, aminopropyl-silicic acid, poly-L-lysine, cellulose, cellulose salt or their derivatives, adipic acid, gelatin, pectin, arginine or their polymer, gluconic acid, lactone, sodium caseinate, vinyl acetate, starch or its derivatives, elastin, acrylamide, acrylamide polymer or their derivatives, gelan gum, carbopol, glutaraldehyde, and acrylate polymer.

12. The kit for a self-molding permanent according to claim 10, wherein the reactive substance is selected from the group consisting of polyalkylene glycol, chito acid and maleic acid.

13. The kit for a self-molding permanent according to claim 10, wherein the reducing composition (a) contains a molding stimulant and a reactive substance in a 1:0.1~5 of weight ratio.

14. The kit for a self-molding permanent according to claim 1 or claim 2, wherein the bivalent metal is magnesium, calcium, barium, strontium, zinc and iron (II).

15. The kit for a self-molding permanent according to claim 1 or claim 2, wherein the softening composition (c) has a pH in the range of 2~9.

16. The kit for a self-molding permanent according to claim 1 or claim 2, wherein the softening composition (c) contains a softening agent selected from the group consisting of inorganic acid, organic acid or/and their acid salts and minerals.

17. The kit for a self-molding permanent according to claim 16, wherein the inorganic acid is selected from the group consisting of nitric acid, sulfuric acid, carbonic acid, bicarbonic acid, hydrochloric acid and phosphoric acid.

18. The kit for a self-molding permanent according to claim 16, wherein the organic acid is selected from the group consisting of citric acid, succinic acid and acetic acid.

19. The kit for a self-molding permanent according to claim 16, wherein the minerals is selected from the group consisting of yellow earth, illite, quartz porphyry, bentonite and monmorylonite.

20. The kit for a self-molding permanent according to claim 16, wherein the softening agent is contained in the range of 0.1~50 weight parts per 1 weight part of the molding stimulant that is added to the reducing composition (a).

21. The kit for a self-molding permanent according to claim 1, wherein the softening agent (c) contains an oxidant selected from the group consisting of peroxides, bromates and peroxy salts and a oxidizing catalyst selected from the group consisting of iron, zinc, copper, cobalt, zirconium, vanadium, manganese and titanium.

22. The kit for a self-molding permanent according to claim 2, wherein the oxidizing composition (d) has a pH in the range of 2~7.

23. The kit for a self-molding permanent according to claim 2, wherein the oxidizing composition (d) contains an oxidant selected from the group consisting of peroxides, bromates and peroxy salts.

24. The kit for a self-molding permanent according to claim 2, wherein the oxidizing composition (d) contains an oxidizing catalyst selected from the group consisting of iron, zinc, copper, cobalt, zirconium, vanadium, manganese and titanium.

25. The kit for a self-molding permanent according to claim 21 or claim 23, wherein the oxidant is contained in the range of 0.1~10 weight parts per 1 weight part of the softening agent added to the softening composition (c).

26. The kit for a self-molding permanent according to claim 21 or claim 24, wherein the oxidizing catalyst is in a powder or in a liquid form that includes a metal or a metal compound of nano-size.

27. The kit for a self-molding permanent according to claim 1 or claim 2, wherein the reducing composition (a) contains 1~25 weight % of reducing agent and 0.1~15 weight % of molding stimulant.

28. The kit for a self-molding permanent according to claim 27, wherein the reducing composition (a) comprises 2~20 weight % of reducing agent, 0.1~15 weight % of molding stimulant, 0.01~3 weight % of reactive substance, 0.0001~5 weight % of reduction catalyst, and 30~90 weight % of deionized water.

29. The kit for a self-molding permanent according to claim 1 or claim 2, wherein the molding composition (b) contains a bivalent metal in 0.1~25 weight % as a metal component.

30. The kit for a self-molding permanent according to claim 29, wherein the molding composition (b) comprises 1~20 weight % of bivalent metal, and 70~98 weight % of deionized water.

31. The kit for a self-molding permanent according to claim 1 or claim 2, wherein the softening composition (c) contains a softening agent in 0.1~25 weight %.

32. The kit for a self-molding permanent according to claim 31, wherein the softening composition (c) comprises 1~20 weight % of softening agent, 1~20 weight % of oxidant, 0.0001~5 weight % of oxidizing catalyst, and 70~98 weight % of deionized water.

33. The kit for a self-molding permanent according to claim 2, wherein the oxidizing composition (d) contains the oxidant in the amount of 0.1~25 weight %.

34. The kit for a self-molding permanent according to claim 31, wherein the oxidizing composition (d) comprises 1~20 weight % of oxidant, 0.0001~5 weight % of oxidizing catalyst, 0.01~20 weight % of ordinary additive and 70~98 weight % of deionized water.

35. A method for treating hair in a free-rod and free-band type permanent, which comprises steps: (1) coating the hair with a reducing composition, wherein the reducing composition comprises a reducing agent, a molding stimulant, and a reduction catalyst comprised of a colloidal-type metal or metal compound having nano-sized particles, wherein the colloidal-type metal or the metal compound is selected from the group consisting of gold, platinum, palladium, rhodium, titanium dioxide, zinc oxide, and vanadium oxide; (2) curling the coated hair; (3) coating the curled hair with a molding composition comprising at least one bivalent metal or metal compound and its soluble salt to form a molding membrane with the molding stimulant in the reducing composition, wherein the at least one bivalent metal or metal compound is present in an amount from 0.001 to 5 weight parts per 1 weight part of the molding stimulant contained in the reducing composition; (4) coating the molded hair with a softening composition to stop the molding action; and (5) washing the hair coated with the softening composition.

36. A method for treating hair in a free-rod and free-band type permanent, which comprises steps: (1) coating the hair with a reducing composition, wherein the reducing composition comprises a reducing agent, a molding stimulant, and a reduction catalyst comprised of a colloidal-type metal or metal compound having nano-sized particles, wherein the colloidal-type metal or the metal compound is selected from the group consisting of gold, platinum, palladium, rhodium, titanium dioxide, zinc oxide, and vanadium oxide; (2) curling the coated hair; (3) coating the curled hair with a molding composition comprising at least one bivalent metal or metal compound and its soluble salt to form a molding membrane with the molding stimulant in the reducing composition, wherein the at least one bivalent metal or metal compound is present in an amount from 0.001 to 5 weight parts per 1 weight part of the molding stimulant contained in the reducing composition; (4) coating the molded hair with an oxidizing composition and then coating the oxidized hair with a softening composition to stop the molding action; and (5) washing the hair coated with the softening composition.

37. The method for treating hair according to claim 35 or claim 36, wherein the reducing composition contains a reducing agent in 1~25 weight % and a molding stimulant in 0.1~15 weight %.

38. The method for treating hair according to claim 35, wherein the reducing composition contains the reducing agent in 1~25 weight % and the molding stimulant in 0.1~15 weight %; the molding composition contains 0.1~25 weight % of bivalent metal as a metal component; and the softening composition contains 0.1~25 weight % of softening agent.

39. The method for treating hair according to claim 36, wherein the reducing composition contains the reducing agent in 1~25 weight % and the molding stimulant in 0.1~15 weight %; the molding composition contains 0.1~25 weight % of bivalent metal as a metal component; the softening composition contains 0.1~25 weight % of softening agent; and the oxidizing composition contains 0.1~25 weight % of oxidant.

40. The method for treating hair according to claim 35 or claim 36, wherein the time period contacting the permanent agent on the hair is adjusted to 1~40 minutes.

41. The method for treating hair according to claim 35 or claim 36, wherein the step curling hair (2) is accomplished by the hand or by using a curling device to design the hair.

42. The method for treating hair according to claim 41, wherein the curling device is detached from the hair after coating a molding composition.

43. The method for treating hair according to claim 35 or claim 36, wherein the reducing composition (a) has a pH in the range of 4~11.

44. The method for treating hair according to claim 35 or claim 36, wherein the reducing composition contains a reducing agent having a functional group selected from the group consisting of sulfide, bisulfide, thiol, cyanide, thiocyanide, hydroxide, sulfite and bisulfite.

45. The method for treating hair according to claim 35 or claim 36, wherein the molding stimulant is selected from the group consisting of algin, alginic acid, alginate, alginic acid salt and their derivatives.

46. The method for treating hair according to claim 35 or claim 36, wherein the reducing composition contains a reducing agent and a molding stimulant in a 1:0.01~1 of weight ratio.

47. The method for treating hair according to claim 35 or claim 36, wherein the reducing composition has the viscosity in the range of 6,000~60,000 cP.

48. The method for treating hair according to claim 35 or claim 36, wherein the reducing composition contains a reactive substance having a reactive group that is selected from the group consisting of hydroxyl (—OH), carboxylic acid (—COOH), ketone (—CO), carboxylate (—COOR) and aldehyde (—COH).

49. The method for treating hair according to claim 48, wherein the reactive substance is selected from the group consisting of polyalkylene glycol, chito acid and maleic acid.

50. The method for treating hair according to claim 35 or claim 36, wherein the reducing composition contains a reduction catalyst selected from the group consisting of gold, platinum, palladium, rhodium, hydrides, hydroxides, oxalic acid and ascorbic acid.

51. The method for treating hair according to claim 35 or claim 36, wherein the reduction catalyst is in a powder or in a liquid form that includes a metal or a metal compound selected from the group consisting of gold, platinum, palladium and rhodium of nano-size.

52. The method for treating hair according to claim 35 or claim 36, wherein the molding composition has a pH in the range of 2~12.

53. The method for treating hair according to claim 35 or claim 36, wherein the softening composition has a pH in the range of 2~9.

54. The method for treating hair according to claim 35 or claim 36, wherein the softening composition contains a softening agent selected from the group consisting of inorganic acid, organic acid or/and their acid salts and minerals.

55. The method for treating hair according to claim 35, wherein the softening agent further contains an oxidant selected from the group consisting of peroxides, bromates and peroxy salts and an oxidizing catalyst selected from the group consisting of iron, zinc, copper, cobalt, zirconium, vanadium, manganese and titanium.

56. The method for treating hair according to claim 36, wherein the oxidizing composition contains an oxidant selected from the group consisting of peroxides, bromates and peroxy salts.

57. The method for treating hair according to claim 36, wherein the oxidizing composition contains an oxidizing catalyst selected from the group consisting of iron, zinc, copper, cobalt, zirconium, vanadium, manganese and titanium.

58. The method for treating hair according to claim 55 or claim 56, wherein the oxidant is added in the range of 0.1~10 weight parts per 1 weight part of softening agent contained in the softening composition.

59. The method for treating hair according to claim 55 or claim 57, wherein the oxidizing catalyst is a powder or in a liquid form that includes a metal or a metal compound of nano-size.

60. The method for treating hair according to claim 35 or claim 36, wherein the step molding hair (3) is accomplished by heating at 30~60° C.

61. The kit for a self-molding permanent according to claim 1 or claim 2, wherein the molding composition (b) has a pH in the range of 2~12.

* * * * *